(12) United States Patent
Igaki et al.

(10) Patent No.: US 8,333,793 B2
(45) Date of Patent: Dec. 18, 2012

(54) HEAT AND STEAM GENERATOR FOR EYE APPLICATION

(75) Inventors: Michihito Igaki, Tokyo (JP); Kyoko Tagami, Tokyo (JP)

(73) Assignee: Kao Corporation, Tokyo (JP)

( * ) Notice: Subject to any disclaimer, the term of this patent is extended or adjusted under 35 U.S.C. 154(b) by 766 days.

(21) Appl. No.: 12/295,314

(22) PCT Filed: Mar. 30, 2007

(86) PCT No.: PCT/JP2007/057141
§ 371 (c)(1),
(2), (4) Date: Oct. 16, 2008

(87) PCT Pub. No.: WO2007/114352
PCT Pub. Date: Oct. 11, 2007

(65) Prior Publication Data
US 2010/0010598 A1    Jan. 14, 2010

(30) Foreign Application Priority Data

Mar. 31, 2006 (JP) ................. 2006-097590

(51) Int. Cl.
*A61F 2/00* (2006.01)
*A24B 3/14* (2006.01)
*A24F 1/22* (2006.01)
*A24F 1/32* (2006.01)
*A24F 13/04* (2006.01)
*H01M 8/06* (2006.01)

(52) U.S. Cl. ......... 607/109; 131/369; 131/194; 429/410

(58) Field of Classification Search ................. 607/109; 131/194, 369; 429/410
See application file for complete search history.

(56) References Cited

U.S. PATENT DOCUMENTS

| 6,409,746 | B1 | 6/2002 | Igaki et al. |
| 6,629,964 | B1 | 10/2003 | Ono et al. |
| 6,823,860 | B2 | 11/2004 | Igaki et al. |
| 7,036,503 | B2 * | 5/2006 | Miyazawa et al. ........ 128/201.13 |
| 7,074,234 | B2 * | 7/2006 | Tone et al. ..................... 607/108 |

(Continued)

FOREIGN PATENT DOCUMENTS
EP    1 090 614 A2    4/2001
(Continued)

OTHER PUBLICATIONS

U.S. Appl. No. 12/626,237, filed Nov. 25, 2009, Igaki, et al.

(Continued)

*Primary Examiner* — Nicholas Lucchesi
*Assistant Examiner* — Ian Holloway
(74) *Attorney, Agent, or Firm* — Oblon, Spivak, McClelland, Maier & Neustadt, L.L.P.

(57) ABSTRACT

A heat and steam generator for eye application includes a heat and steam generating member making use of oxidative reaction of an oxidizable metal and is adapted to supply steam to eyes and surroundings. The heat and steam generator is adapted to release steam from its side brought into contact with eyes and surroundings for a period of 1 to 30 minutes to maintain the skin surface temperature to which it is applied at 34° C. to 43° C. over a period of 1 to 120 minutes. The heat and steam generator has a stiffness of 0.01 to 10 N/7 cm-width. The heat and steam generator is effective in improving near triad causing reduction in vision.

18 Claims, 14 Drawing Sheets

U.S. PATENT DOCUMENTS

| | | | |
|---|---|---|---|
| 7,568,255 B1* | 8/2009 | Krebs | 15/104.93 |
| 7,749,401 B2* | 7/2010 | Roselle et al. | 252/8.91 |
| 2004/0035410 A1 | 2/2004 | Igaki et al. | |
| 2004/0098072 A1 | 5/2004 | Tone et al. | |
| 2005/0192653 A1* | 9/2005 | Tsunakawa et al. | 607/109 |
| 2007/0020412 A1 | 1/2007 | Kumamoto et al. | |
| 2007/0079470 A1* | 4/2007 | Rippl et al. | 15/320 |
| 2007/0110790 A1 | 5/2007 | Igaki et al. | |

FOREIGN PATENT DOCUMENTS

| | | |
|---|---|---|
| EP | 1 090 614 A3 | 4/2001 |
| EP | 1 147 752 A1 | 10/2001 |
| EP | 1 393 699 A1 | 3/2004 |
| JP | 2002 65714 | 3/2002 |
| JP | 2002 78728 | 3/2002 |
| WO | WO 99/51174 | 10/1999 |
| WO | WO 2005/011543 A1 | 2/2005 |
| WO | 2005 058213 | 6/2005 |

OTHER PUBLICATIONS

Chinese Office Action issued Aug. 31, 2010, in Chinese Patent Application No. 200780011912.7 (with English-language translation).

Extended European Search Report issued Mar. 14, 2011, in Patent Application No. 07740577.7.

\* cited by examiner

US 8,333,793 B2

HEAT AND STEAM GENERATOR FOR EYE APPLICATION

TECHNICAL FIELD

The present invention relates to a heat and steam generator for eye application that is effective on improvement of near triad causing a decrease in vision and relief from dry eye conditions.

BACKGROUND ART

Causes of reduction in vision (blurred vision, hazy vision, indistinct vision, dry eye) and eyestrain are known as near (reflex) triad. The near triad includes (1) reduction of accommodation, (2) reduction of pupillary response, and (3) convergence response abnormality. Reduction of accommodation is attributed to hypertonicity of the ciliary muscle or lens hardening. Reduction in pupillary response is caused by a decrease in pupillary constriction rate or decrease in response speed. Convergence response abnormality is attributed to an abnormal change of pupil position of both eyes. One of the known causes of dry eye is insufficient tear film formation on the corneal surface due to obstruction of meibomian glands.

In this connection, Patent Document 1 assigned to the common assignee of the present invention proposes a vision improving device that supplies steam to the eyes and its surroundings thereby to improve the function of accommodation muscles including ciliary muscle and improve the visual acuity of pseudomyopic eyes or aged eyes. The vision improving device is designed to release steam from its surface at a controlled temperature of 50° C. or lower thereby to recover the vision or reduce bleariness or blur in vision associated with dysfunction of accommodation muscles or accommodative spasm easily and effectively. Patent Document 1 describes the vision improving device as having effects on the improvement of declined accommodation, one of the near triad responses. The publication does not mention, however, whether the proposed vision improving device is effective in improving pupillary response and convergence response, the rest of the near reflex triad.

Patent Document 1 JP 2002-65714A

DISCLOSURE OF THE INVENTION

The present invention relates to a heat and steam generator for eye application (hereinafter simply referred to as a heat and steam generator). The heat and steam generator has a heat and steam generating member that generates heat and steam by making use of oxidative reaction of an oxidizable metal and is designed to supply steam to the eyes and its surroundings. The heat and steam generator is adapted to be applied to the eyes and its surroundings on its one side and release steam for a period of 1 to 30 minutes from that side to maintain the skin surface temperature to which it is applied at 34° C. to 43° C. over a period of 1 to 120 minutes. The heat and steam generator has a stiffness of 0.01 to 10N/7 cm-width.

DETAILED DESCRIPTION OF THE INVENTION

The present invention will be described based on its preferred embodiments with reference to the accompanying drawing. The present invention relates to a heat and steam generator for eye application that is effective in improving the near triad causative of decrease in vision and dry eye.

The heat and steam generator according to the invention is used to apply heat accompanied by steam (hereinafter also referred to as "heat and steam") to a broad area including the eyes and its surroundings. The heat and steam generator includes a holder and a heat and steam generating member held in the holder. The holder has a steam permeable portion allowing steam generated by the heat and steam generating member to pass therethrough. For example, the holder is a flat container having a first side having an air permeable portion in at least a part thereof and a second side having an air permeable portion in at least a part thereof on the opposite side to the first side. Steam is allowed to pass through at least through the side brought into contact with the skin. The air permeance of the first side designed to be brought into contact with the skin is preferably 0.01 to 15000 sec, and that of the second side is preferably 100 to 60000 sec. Otherwise, the holder is a flat container having an air permeable side and an opposing air-impermeable side and is designed to allow steam to pass through the air permeable side in contact with the skin.

The heat and steam generator of the invention supplies heat accompanied by steam to a broad area including the eyes and its surroundings. As used herein, the term "surroundings (of eyes)" is intended to indicate the outer area of opened lid fissures, including eye pits and the surroundings of eye pits. The phrase "supply heat" as used herein is intended to include a mode in which the heat and steam generator is brought into direct contact with the skin to give heat to the skin and a mode in which the heat and steam generator is brought into indirect contact with the skin via an intervening, steam-permeable material to give heat to the skin.

Figure 1:
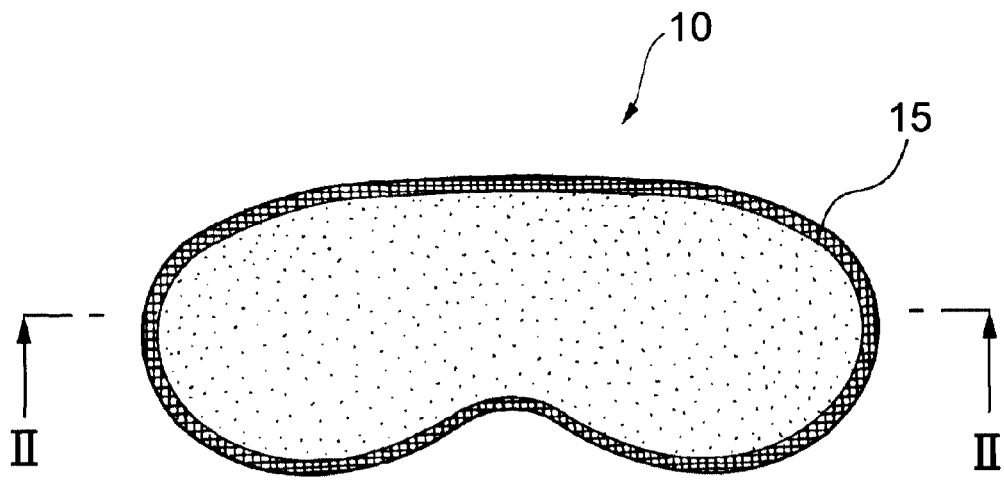
FIG. 1 is a plan of an embodiment of a heat and steam generating sheet for eye application according to the invention.
Figure 2:
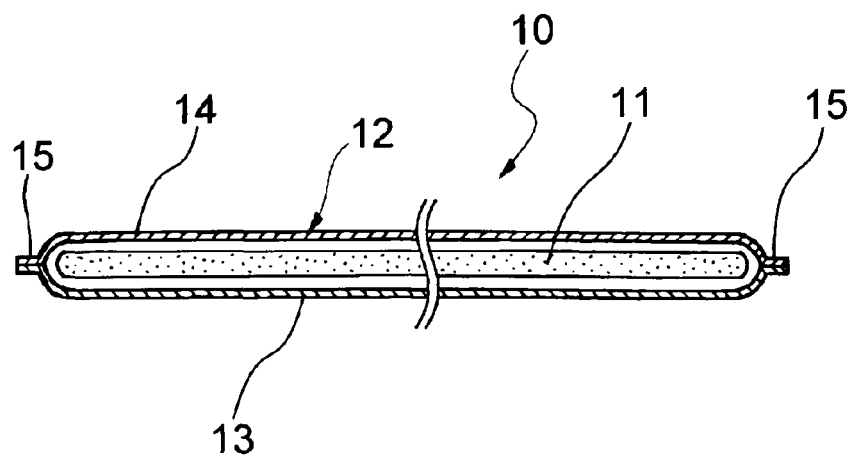
FIG. 2 is a cross-section taken along line II-II of FIG. 1.

FIG. 1 illustrates a plan of a heat and steam generating sheet for eye application as a preferred embodiment of the heat and steam generator of the present invention. FIG. 2 is a cross-section of the heat and steam generating sheet taken along line II-II in FIG. 1. The heat and steam generating sheet 10 shown in FIG. 1 has a generally flat eye-mask shape of size enough to cover the above-identified surroundings. The heat and steam generating sheet 10 includes a heat and steam generating member 11 and a holder 12 holding therein the heat and steam generating member 11. The holder 12 is a flat container formed of a plurality of sheets to provide a closed space in which the heat and steam generating member 11 is put. The flat holder 12 has a first side 13 that is to face the skin of a wearer and a second side 14 that is not to face the skin of a wearer and opposite to the first side 13.

The heat and steam generating member 11 contains an oxidizable metal. The heat and steam generating member 11 is a part that generates steam of prescribed elevated temperature by making use of the heat accompanying the oxidation reaction between the oxidizable metal and oxygen.

At least part of the first side 13 is permeable to air and steam, namely air permeable. At least part of the second side 14 is also permeable to air and steam, namely air permeable. When both the first and second sides are air permeable as in the present embodiment, the heat and steam generating sheet 10 is preferably designed to release steam through at least the first side 13 facing the eyes and the surroundings. For example, it is preferred that the air permeance (JIS P8117) of the second side 14 is equal to or larger than that of the first side 13 so as to make the release of the generated steam through the first side 13. The second side 14, which is air permeable in the present embodiment, may be substantially impermeable to air and steam, namely air impermeable.

The heat and steam generating sheet 10 is used with the first side 13 facing the skin (eyes) of a wearer and the second side 14 facing outside. Steam generated by the heat of the heat and steam generating member 11 is applied to the skin to be treated through the first side 13.

Both the first side 13 and the second side 14 of the heat and steam generating sheet are formed of a sheet material. At the perimeter of the holder 12 in the heat and steam generating sheet 10, the sheet materials forming the first side 13 and the second side 14 are joined together along their perimeter to form a peripheral seal 15 of closed loop. The peripheral seal 15 is continuous. The sheet materials forming the first side 13 and the second side 14 are not bonded to each other inside the peripheral seal 15. There is thus provided a single closed space in which the heat and steam generating member 11 is held.

In the first embodiment shown in FIG. 2, the number of the heat and steam generating member 11 put in the holder 12 is one. The heat and steam generating member 11 put in the holder occupies almost the whole space of the holder 12. That is, the holder 12 contains one heat and steam generating member 11, and the heat and steam generating member 11 occupies almost the whole space of the holder 12 except the peripheral seal 15. So configured, the heat and steam generating sheet 10 is applicable over a broader area including the eyes and its surroundings than the vision improving device of Patent Document 1 cited above. As a result, muscles around eyes involved in the near reflex including not only ciliary muscle but the iris and orbicularis oculi muscle and so on are warmed by heat and steam to improve blood circulation, which results in manifestation of marked effects in improving the near triad as will be demonstrated in Examples given later. When worn by a wearer suffering from meibomian gland dysfunction, the sheet 10 warms meibomian glands by the heat and steam, whereby the viscous secretion obstructing the meibomian bland is melted to allow lipid to be normally secreted from meibomian glands. The lipid covers the outer surface of a tear film to retard evaporation and prevent dry eye. As a result, remarkable effects in alleviating dry eye symptoms attributed to excessive evaporation of tear are produced as will be demonstrated in the Examples given later.

Besides being capable of supplying steam over a broad area of the eyes and its surroundings, the heat and steam generating sheet 10 of the first embodiment continues generating steam from its first side 13, the side facing the eyes and its surroundings, for a period of from 1 to 30 minutes, preferably 5 to 25 minutes, from the contact with oxygen. Furthermore, the heat and steam generating sheet 10 increases the skin surface temperature to which it is applied to 34° C. at the lowest and 43° C. at the highest, preferably 36° C. at the lowest and 41° C. at the highest, and keeps the so increased skin temperature for 1 minutes at the shortest and 120 minutes at the longest while it is worn. As a result, further enhanced effects in improving the near triad responses and alleviating dry eye conditions are obtained. Because skin surface temperature does not fall rapidly even after the end of steam generation owing to the heat insulating properties of the skin, the duration of the skin surface temperature is longer than the duration of steam generation.

Figure 3:
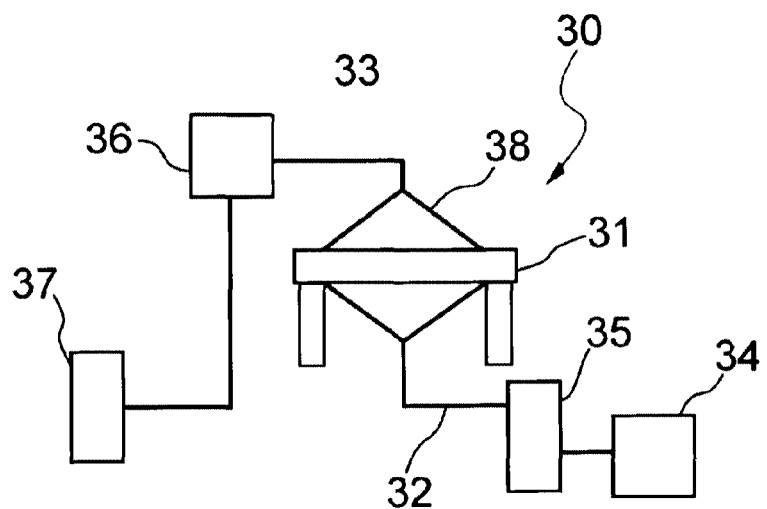
FIG. 3 is a sketch of equipment for measuring the duration of steam generation by a heat and steam generating sheet for eye application of the invention.

In the present invention the duration of steam generation is measured by use of the equipment 30 illustrated in FIG. 3. The equipment 30 of FIG. 3 has an aluminum-made measuring chamber 31 (capacity: 2.1 liter), an inlet tube 32 for introducing dehumidified air (humidity: <2%; flow rate: 2.1 l/min) connected to the lower part of the measuring chamber 31, and an outlet tube 33 for releasing air connected to the upper part of the measuring chamber 31. The inlet tube 32 is equipped with an inlet thermohygrometer 34 and an inlet flow meter 35. The outlet tube 33 is equipped with an outlet thermohygrometer 36 and an outlet flow meter 37. The measuring chamber 31 is equipped with a thermometer (thermistor) 38. The thermometer 38 has a temperature resolution of about 0.01° C. A heat and steam generating sheet 1 is taken out of a package at a measuring environment temperature 30° C. (±1° C.) and placed in the measuring chamber 31 with its steam release side up. The thermometer 38 having a metal ball weighing 4.5 g is put on the sheet 10. Dehumidified air is let in from the lower part of the chamber 31. The difference of absolute humidity between the air before entering the chamber 31 and the air having flowed from the chamber 31 is obtained from the temperatures and humidities measured with the inlet thermohygrometer 34 and the outlet thermohygrometer 36. The amount of steam generated and released from the sheet 1 is calculated from the flow rates measured with the inlet flow meter 35 and the outlet flow meter 37. JP 2004-73688A commonly assigned to the assignee of the present invention can be referred to for the details of the equipment. The skin surface temperature can be measured with a thermistor-thermometer LTST08-12 from Gram Corp. The skin temperature is measured at an upper eyelid. The measuring environment temperature is 20° C. The measuring interval is 10 seconds.

The heat and steam generating sheet 10 of the first embodiment has properly controlled air permeances through the first side 13 and the second side 14 so that steam may be released preferentially through the first side 13. In addition to this, the heat and steam generating sheet 10 has properly controlled air permeances through the first side 13 and the second side 14 so that the above recited duration of steam generation may be achieved easily and that the above recited skin surface temperature may be reached easily. Specifically, the air permeance of the second side 14 is designed to be equal to or higher than that of the first side 13. The term "air permeance" as used herein is a value measured in accordance with JIS P8117 (ISO 5636/5—Part 5), which is defined to be the time required for 100 ml of air to pass through an area of 6.42 cm$^2$. A higher air permeance means more time needed for air passage, i.e., lower air permeability. A lower air permeance means higher air permeability. Air permeance as defined above and air permeability are in a converse relation. Comparing the air permeability between the first side 13 and the second side 14, it is preferred that the first side 13 has an equal or higher air permeability than the second side 14. Proper adjustment of the air permeability balance between the first side 13 and the second side 14 enables uniform supply of heat and steam to the eyes and its surroundings.

The holder 12 has a flat shape having the air permeable first side 13 and the opposite, second side 14 and is designed to release heat and steam through the air permeable first side 13. The second side 14 has an equal or higher air permeance to or than the first side 13. As the air permeance increases extremely, the side becomes less and less air permeable. That is, when the air permeance of the second side 14 is extremely high, the second side 14 is an air impermeable side.

As a result of study, the present inventors have found that, when the second side 14 which is air permeable has an air permeance preferably of 100 seconds or more, more preferably 100 to 60,000 seconds, even more preferably 1,000 to 60,000 seconds, further more preferably 4,000 to 40,000 seconds, even more preferably 5,000 to 25,000 seconds, air is preferentially let in the holder 12 through the second side 14 whereas steam is preferentially released through the first side 13. It follows that air is stably supplied throughout the heat and steam generating member 11 to cause the heat and steam generating member 11 to generate heat uniformly. The steam generated by the thus generated heat is uniformly applied to the skin of a wearer through the first side 13.

A water vapor transmission rate (JIS Z0208, measured at 40° C. and 90% RH, hereinafter the same) is known as another measure of air permeability of a sheet material. By and large, steam permeability of an air permeable sheet in a heat generating implement such as a disposable body warmer is represented exclusively in terms of water vapor transmission rate. In the present embodiment, in contrast, air permeability is evaluated by air permeance but not by water vapor transmission rate. Adjusting the air permeance values allows for preferential steam release from the first side 13 even where the second side has air permeability. The reason for this, the inventors believe, is that the measuring conditions differ between air permeance and water vapor transmission rate. Water vapor transmission rate is measured under hydrostatic pressure, whereas air permeance is measured under pressure. Since the heat and steam generating sheet 10 generates steam in the inside thereof by the heat generated by the heat and steam generating member 11, the holder 12 has a positive internal pressure. Therefore, air permeance measured under pressure is considered better suited to the practice of the invention than water vapor transmission rate measured under hydrostatic pressure to evaluate permeability to steam.

As stated previously, when the second side 14 facing outside is air permeable, the amount of steam released through the first side 13 and that through the second side 14 depend on the air permeance of the respective sides. For example, even when the second side 14 lets in outer air, the amount of steam released outside can be lower through the second side 14 than through the first side 13. The amount of steam released from the second side 14 is not always large even if the second side 14 lets in much air. This is because both sides of the holder 12 have air permeability. In other words, the air permeance balance between the first side 13 and the second side 14 influences the amount of air let in and the amount of steam let out through the second side 14. Then, in order to suppress steam release from the second side 14 while securing inflow of air through that side, the following air permeance balances are preferred. In the cases where the air permeance of the second side 14 is equal to or greater to some extent than that of first side 13, the air permeance of the former is preferably not greater than three times that of the latter.

In the cases where the air permeance of the second side 14 is considerably larger than that of the first side 13, the air permeance of the former is preferably not less than five times, more preferably ten or more times, even more preferably a hundred or more times, that of the latter. Otherwise, it is also preferred that the ratio of the air permeance of the second side 14 to the air permeance of the first side 13 is preferably 0.5 or smaller, more preferably 0.2 or smaller. When these conditions are satisfied, release of steam from the second side 14 is further decreased, while release of steam from the first side 13 is further increased. When the second side 14 is air impermeable, air inflow into the holder 12 and steam release from the holder 12 are exclusively through the first side 13.

The air permeance of the first side 13 is preferably 0.01 to 15,000 seconds, more preferably 0.01 to 10,000 seconds, irrespective of whether the second side 14 is air permeable or impermeable. In the present invention it is preferred that the air permeance of the first side 13 through which steam should pass is set first and then the conditions of the second side 14 so as to the result in desired temperature and amount of steam generation.

It is preferred that the first side 13 and the second side 14 have respectively controlled water vapor transmission rates (hereinafter abbreviated as "WVTR") as well as respectively controlled air permeances to help the heat and steam generating member 11 to exhibit good heat generation characteristics thereby making it easier to achieve the above recited duration of the heat and steam generation and range of skin surface temperature. WVTR is associated with the degree of air inflow while air permeance is associated with the degree of steam release. This is because the former is measured under hydrostatic pressure as is understood from the measuring conditions previously described and well suited to evaluate ease of air passage under atmospheric pressure. The first side 13 preferably has a WVTR of 100 g/(m²·24 hr) or higher, more preferably 100 to 20,000 g/(m²·24 hr), even more preferably 200 to 12,000 g/(m²·24 hr), irrespective of whether the second side 14 is air permeable or impermeable. Where the second side 14 is air impermeable, the WVTR of the first side 13 is preferably 100 to 20,000 g/(m²·24 hr), nevertheless. When the second side 14 is air permeable, on the other hand, the WVTR of the second side 14 is preferably 100 to 6,000 g/(m²·24 hr), more preferably 200 to 5,000 g/(m²·24 hr). WVTR is measured in accordance with JIS Z0208 using the calcium chloride method under condition A (25° C.±0.5° C., 90%±2% RH) or condition B (40° C.±0.5° C., 90%±2% RH). The choice between the conditions A and B depends on the WVTR values. In general, the condition B is chosen for measuring large WVTRs. Whichever condition is chosen, it is difficult to measure WVTRs above 12,000 g/(m²·24 hr) in relations with water vapor absorption weight. In the practice of the invention, sheet materials having a WVTR above 12,000 g/(m²·24 hr) also can be used.

As stated, air permeance and WVTR are typical physical properties representing gas permeability of sheet materials. The correlation between them varies depending on the sheet material. Some sheet materials show a correlation therebetween, and others do not. Therefore, it is of technical significance to set preferred ranges of WVTRs as well as air permeances for the first side 13 and the second side 14.

The distance between the heat and steam generating sheet 10 and the skin is also of importance in order to efficiently apply the heat and steam generated by the sheet 10 to the eyes and its surroundings thereby to raise the skin surface temperature to the above recited range. To properly set the distance allows for applying heat and steam of proper temperature and amount to the eyes and its surroundings and give a wearer comfort. From this point of view, the stiffness of the heat and steam generating sheet 10 of the present embodiment should be confined within an adequate range so as to maintain a proper distance between the sheet 10 and the skin. Specifically, the stiffness of the heat and steam generating sheet 10 is 0.01 to 10N/7 cm-width, preferably 0.03 to 8N/7 cm-width, more preferably 0.05 to 5N/7 cm-width.

The heat and steam generating sheet 10 can have its stiffness controlled within the recited range by appropriately selecting the material and thickness of the sheets making the first side 13 and the second side 14 or the kind and amount of the material making the heat and steam generating member 11.

Figure 4:
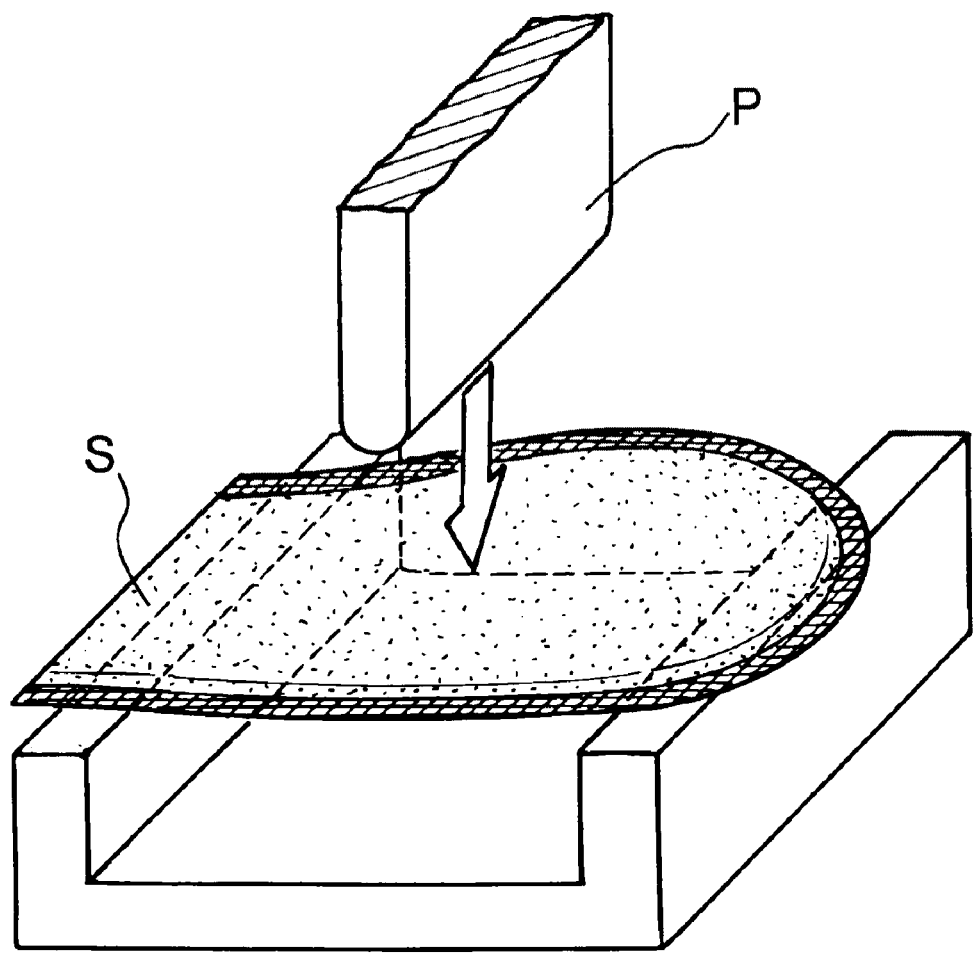
FIG. 4 illustrates the method of measuring stiffness of a heat and steam generating sheet for eye application.

In the invention, the stiffness of the heat and steam generating sheet 10 is measured using a bending strength tester RTA-500 (trade name) from Orientec Co., Ltd. As illustrated in FIG. 4, the heat and steam generating sheet 10 is cut into halves along its vertical centerline L (see FIG. 12), one of which is used as a specimen S. When there is a fear of the heat and steam generating member 11 spilling from the cut area, the cut area is sealed, e.g., with adhesive tape. The portion of the specimen S where the heat and steam generating member 11 exists is supported at the opposite ends thereof with a span of 80 mm. A platy penetrator blade P with a width of 50 mm and a tip radius of 5 mm is moved downward at the center of the specimen S at a crosshead speed of 20 mm/min, and the maximum resistance encountered by the penetrator blade P as it moves is taken as a stiffness. The penetrator blade P is set with its width direction coincident with the vertical direction of the specimen S. When the measured value differs depending on which side of the specimen S (the first side 13 or the second side 14) the load is imposed, an average of the two values is taken as a stiffness of the specimen S.

As previously described, each of the first side 13 and the second side 14 of the heat and steam generating sheet 10 is formed of a sheet material. The kind of the sheet material to be used is selected as appropriate, taking into consideration air permeance, WVTR, texture, feel to the touch, strength, powder (e.g., oxidizable metal powder) spill resistance, and the like. Melt-blown nonwovens and moisture permeable films are suitable sheet materials in terms of air permeance control and powder spill resistance. Synthetic papers are also preferably used. A moisture permeable film is obtainable by melt molding a mixture of a thermoplastic resin and an organic or inorganic filler incompatible with the resin into film and uniaxially or biaxially stretching the film to develop a finely porous structure. Spun-bonded nonwovens are suitable as a material imparting strength. Thermal bonded nonwovens are suitable as a material for improving texture. Sheet materials having different air permeances and WVTRs can be combined to make a laminate sheet. Use of such a laminate sheet enables free control of air permeance and WVTR of each air permeable side. The laminate sheet is exemplified by a three ply sheet having a spun-bonded nonwoven fabric as an innermost layer, a melt-blown nonwoven fabric as an intermediate layer, and a thermal bonded nonwoven fabric as an outermost layer.

While the sheet defining each side of the holder 12 is depicted in FIG. 2 as having a single ply structure for the sake of simplicity, these sheets may be a single ply sheet or a multi-ply sheet having two or more of the above described various sheet materials. The same applies to FIG. 13 described later. In the case when the first side and/or the second side of the holder 12 is/are formed of a two ply laminate sheet(s), a moisture permeable or impermeable film can be used as an inner sheet, and a nonwoven fabric (e.g., a nonwoven fabric 13a illustrated in FIGS. 5(a) and 5(b) hereinafter described) can be used as an outer sheet.

Figure 5A:
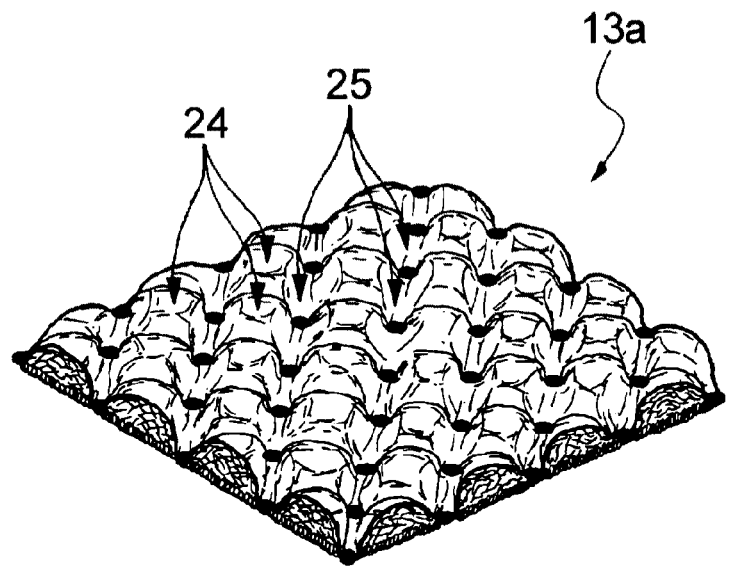
FIG. 5 illustrates a fragmentary enlarged view of nonwoven fabric suited for use in a heat and steam generating sheet for eye application of the invention.
Figure 5B:
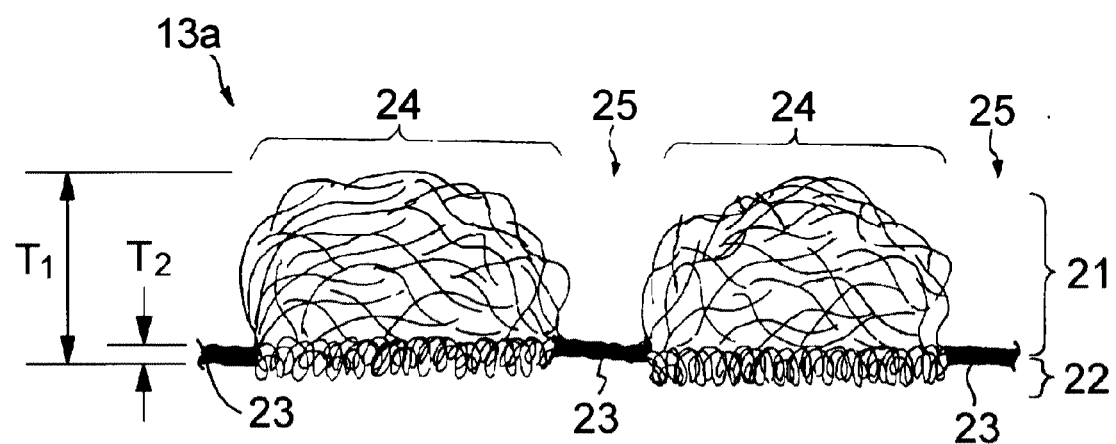

FIGS. 5(a) and 5(b) illustrate a fragmentary enlarged view of a nonwoven fabric 13a defining the outermost surface of the first side 13 of the heat and steam generating sheet 10 of the present embodiment. The nonwoven fabric 13a has a first fiber layer 21 inclusive of one of the surfaces and a second fiber layer 22 inclusive of the other surface. The first fiber layer 21 and the second fiber layer 22 are superposed on each other and partly joined, forming a large number of protrusions 24 and depressions 25 on the side of the first fiber layer 21. The side of the first fiber layer 21 is used as the outermost surface of the first side 13. The first fiber layer 21 and the second fiber layer 22 are formed of respective fiber aggregates. As illustrated, the bonds 23 between the first fiber layer 21 and the second fiber layer 22 are formed by densification by heat and/or pressure application so that they are thinner and denser than the other parts of the nonwoven fabric 13a. As a result, the nonwoven fabric 13a has a large number of protrusions 24 discretely arranged on the side of the first fiber layer 21 in a prescribed pattern and a large number of depressions 25 formed on the bonds 23. The first fiber layer 21 of the nonwoven fabric 13a therefore has an uneven surface topography formed of the protrusions 24 and the depressions 25. The shape of the individual protrusions and depressions is not limited to circular dots of substantially uniform size as illustrated in FIG. 5(a) and may be a combination of a plurality of shapes such as circles of different sizes, elongated circles, and ridges as long as a comfort to the wearer is secured. The protrusions and depressions may be arranged in a random pattern. The protrusions 24 are filled with fibers. The side of the first fiber layer 21 is used as the outermost surface of the first side 13, i.e., the skin (eye) facing side of the heat and steam generating sheet 10. Unlike the surface of the first fiber layer 21, the second fiber layer 22 has a generally flat surface.

While the heat and steam generating sheet 10 is in use, the first fiber layer 21, which has the uneven surface topography, is in contact with the wearer's skin mostly on its protrusions 24. That is, the first fiber layer 21 comes into contact with the wearer's skin not all over the area but in parts by a point contact on the protrusions 24 made of a fiber aggregate to provide comfort to wear with good cushioning and high bulkiness.

The heat and steam generating sheet 10 having the nonwoven fabric 13a illustrated in FIGS. 5(a) and 5(b) has a reduced contact area with the wearer's eyes and its surroundings owing to the uneven surface topography of the first fiber layer 21, which prevents skin overhydration during wear. The steam at a prescribed elevated temperature generated by the heat and steam generating sheet 10 can efficiently be applied to the wearer's eyes and its surroundings because the protrusions 24 serve as a spacer between the sheet 10 and the skin of the eyes and its surroundings. Moreover, the protrusions 24 as a spacer provide a space for permitting air to flow between the sheet 10 and the skin of the eyes and its surroundings. As a result, air is let in smoothly from the first side 13, which is brought into direct contact with the skin of the eyes and its surroundings, assuring stable continuation of heat and steam generation.

Taking the above effects into consideration, it is preferred that the protrusions 24 have a thickness T1 (see FIG. 5(b)) of 1 to 10 mm; the depressions 25 have a thickness T2 (see FIG. 5(b)) of 0.01 to 5 mm, more preferably 0.1 to 1 mm; and T1/T2 is 2 to 50, more preferably 2 to 20. It is also preferred for the same considerations that the ratio of the total area of the bonds 23 to the area of the first nonwoven fabric 13a (area ratio of the bonds 23 per unit area of the first nonwoven fabric 13a) is 3% to 50%, more preferably 5% to 35%; the area of the individual bonds 23 is 0.1 to 5 mm$^2$, more preferably 0.1 to 1 mm$^2$; and the smallest distance between adjacent protrusions 24 (the distance between the center of a protrusion and the center of an adjacent protrusion) is 0.5 to 15 mm, more preferably 1 to 10 mm.

The thickness T2 of the depressions 25 and the substantial thickness T1 of the protrusions 24 are measured on a photograph or an image of a cross-section of the surface sheet with no pressure applied. In the present invention, the first nonwoven fabric 13a is cut along a line passing the crest of a protrusion 24 and a depression 25, and the cut area profile is observed under a microscope VH-8000 from Keyence Corp. to measure the thickness T2 of the depression 25 and the substantial thickness T1 of the protrusion 24.

The nonwoven fabric 13a preferably has a basis weight of 20 to 200 g/m$^2$, more preferably 40 to 150 g/m$^2$. The basis weight is obtained by cutting a piece of 50 mm by 50 mm or greater size out of the nonwoven fabric 13a, weighing the piece with an electron balance having a minimum readability of 1 mg, and converting the weight to a per unit area basis.

The nonwoven fabric 13a allows for air flow in a horizontal direction (a direction perpendicular to the sheet thickness direction) because of the uneven surface topography of the first fiber layer 21. The air flow is maintained even under a prescribed pressure. Specifically, the nonwoven fabric 13a preferably has an air transmission rate of 10 to 500 ml/(cm$^2$·sec), more preferably 20 to 200 ml/(cm$^2$·sec), in the horizontal direction under a pressure of 50 cN/cm$^2$. When the air transmission rate in a horizontal direction (hereinafter "horizontal air transmission rate") under a pressure of 50 cN/cm$^2$ is 10 ml/(cm$^2$·sec) or more, a horizontal air permeation can be maintained sufficiently, and a space is secured between the fabric 13a and the skin of the eyes and its surroundings through which air is let to flow in, even when the nonwoven fabric 13a is strongly pressed into intimate contact with the wearer's eyes and its surroundings. The nonwoven fabric 13a is therefore no hindrance to the reaction of the heat and steam generating member 11 as compared with common nonwoven fabrics. To put it another way, even if the nonwoven fabric 13a is pressed into intimate contact with the wearer's eyes and its surroundings while the heat and steam generating sheet 10 is worn, a sufficient air flow in the horizontal direction (the direction perpendicular to the sheet thickness direction) can thus be secured, whereby air continues to be supplied to the heat and steam generating member 11, and heat generation continues in a stable manner. Additionally, skin overhydration during wear of the heat and steam generating sheet 10 is prevented effectively, providing assured prevention of discomfort or skin problems such as itches and rash due to overhydration.

Figure 6:
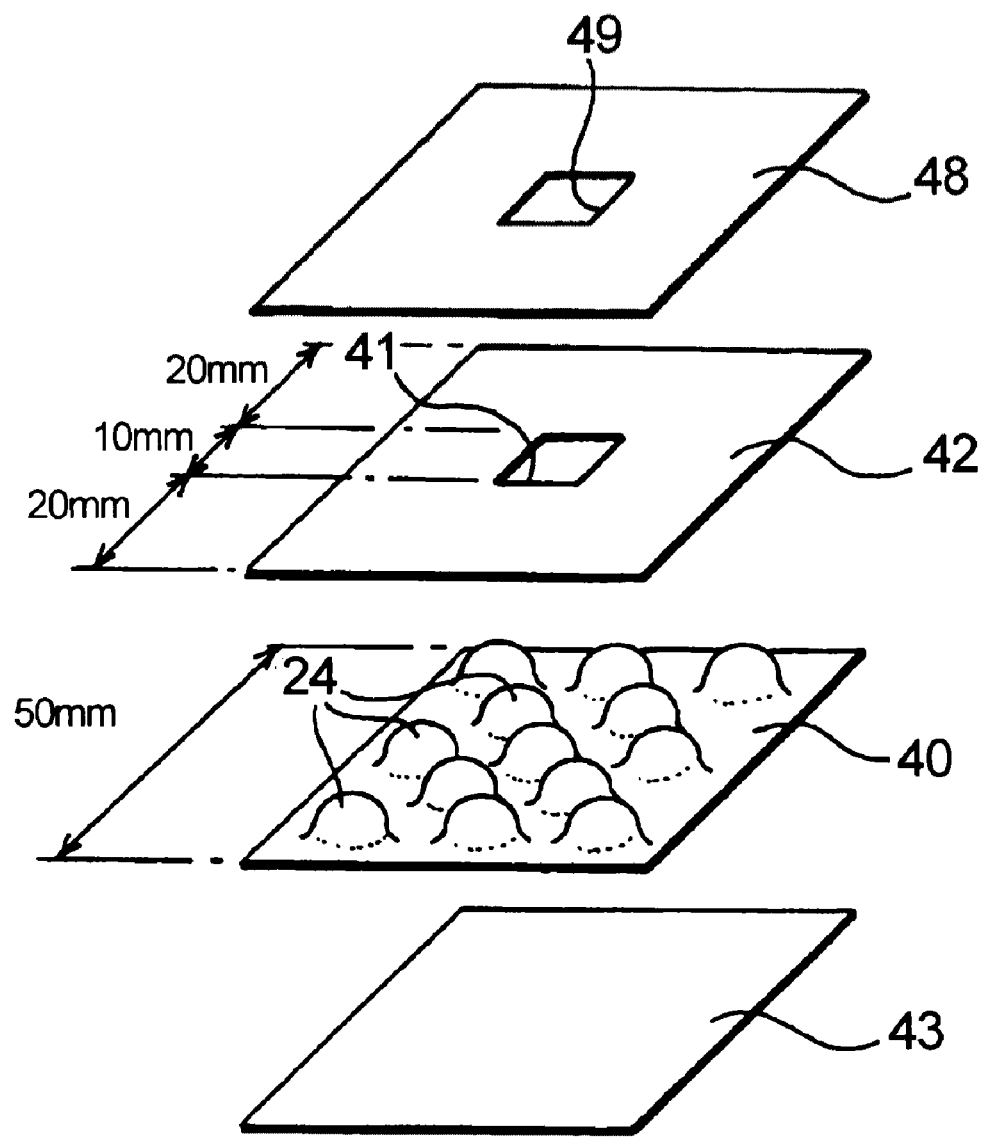
FIG. 6 shows an implement used to measure a horizontal air transmission rate of the nonwoven fabric shown in FIG. 5.
Figure 7:
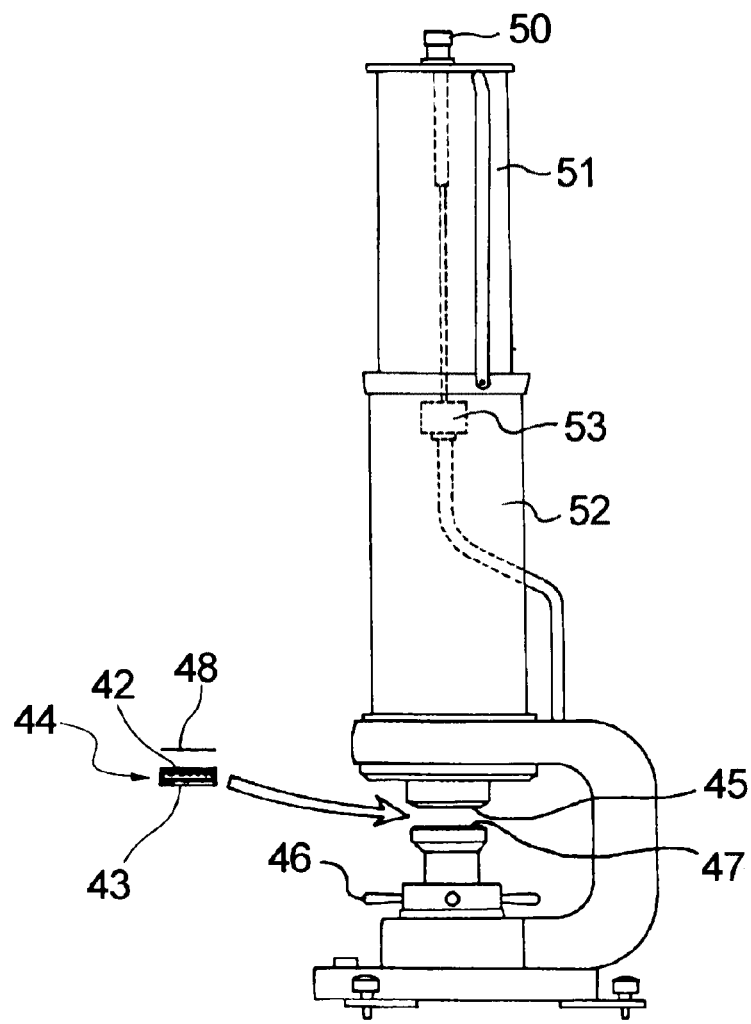
FIG. 7 illustrates an instrument used to measure a horizontal air transmission rate of the nonwoven fabric shown in FIG. 5.

The horizontal air transmission rate under a pressure of 50 cN/cm$^2$ is measured as follows. First of all, the thickness T3 of a nonwoven fabric 13a under a pressure of 50 cN/cm$^2$ is measured beforehand. As illustrated in FIG. 6, a 50 mm-side square is cut out of the nonwoven fabric 13a to provide a specimen 40. The specimen 40 is sandwiched between a first acrylic resin plate 42 of a size 50 mm×50 mm×3 mm and having a 10 mm-side square opening in the central portion thereof and a second acrylic resin plate 43 of the same size as the first acrylic resin plate 42 but having no opening, with the side of the specimen 40 that is to face a wearer (the side with the protrusions 24) facing the first acrylic plate 42, to prepare a stack 44 (see FIG. 7). As illustrated in FIG. 7, the stack 44 is set in a Gurley tester (type B) specified in JIS P8117, under the gasket 45, with the side of the first acrylic resin plate 42 up. The specimen 40 is compressed to the thickness T3. Air is then introduced through the opening 41 into the central part of the specimen 40 kept at the thickness T3, and the time required for introducing 300 ml of air is measured. The amount (ml) of air introduced per unit area (1 cm$^2$ of the opening 41)×1 second is calculated as a horizontal air transmission rate under a load of 50 cN/cm$^2$.

The thickness T3 is measured with a KES compression tester (e.g., KES-BF3, included in "KES-FB" series, from Kato Tech Co., Ltd.). A KES compression tester has an indenter and a receiver, between which a specimen is sandwiched and compression deformed in the thickness direction at a constant rate. A specimen with a greater size than the indenter is cut out of the nonwoven fabric 13a and set on the receiver. The indenter is moved down at a speed of 1.2 mm/min to compress the specimen 40 between the indenter and the receiver. When the compression load reaches 50 cN/cm$^2$, the distance between the indenter and the receiver, which corresponds to the thickness of the specimen 40, is measured to give the thickness T3 of the nonwoven fabric 13a under a load of 50 cN/cm$^2$.

A Gurley tester (B type) that can be used to measure the horizontal air transmission rate is exemplified by Gurley Densometer supplied by Kumagai Riki Kogyo K. K., which is shown in FIG. 7. Compression of the stack 44 and introducing air under compression with the equipment shown in FIG. 7 is carried out as follows. First of all, the stack 44 is positioned under a gasket 45 with the first acrylic plate 42 up, and a clamping handle 46 is turned to adjust the clearance between the gasket 45 and the opposing side 47 so that the specimen 40 may have the intended thickness under load (thickness T3). Numeral 48 in FIGS. 6 and 7 is a silicone plate (hardness: 50) having a 10 mm-side square opening 49 in the central portion thereof, which is inserted between the gasket 45 and the first acrylic plate 42 so that air introduced may not leak through any gap other than the cut edges of the specimen 40. An inner cylinder 51 is lifted by its knob 50 to cause outer air to be sucked into an outer cylinder 52 and then let down into the outer cylinder 52. Thus, 300 ml of air is introduced from an air feed opening (not shown) at the center of the lower side of the gasket 45 into the central portion of the upper side of the specimen 40. The pressure of air introduction depends on the mass of the inner cylinder. The time required for 300 ml of air to be introduced is measured, and the horizontal air transmission rate under 50 cN/cm$^2$ load is calculated. Numeral 53 in FIG. 7 is a photosensor having a combination of a projector and a receptor. A strip with a slit at a predetermined position which is attached to the inner cylinder passes between the projector and the receptor downward to provide signals to a digital counter, whereby the above-defined time is digitally displayed.

The fibers constituting each fiber layer composing the non-woven fabric 13a will be described. The second fiber layer 22 contains three-dimensionally crimped fibers. Three-dimensionally crimped fibers usually have a helical crimp. The second fiber layer 22 may be made solely of the three-dimensionally crimped fibers or may contain other fibers. The other fibers include general thermoplastic resin fibers, regenerated fibers such as rayon, and natural fibers such as cotton. In the case where the second fiber layer 22 contains other fibers in addition to the three-dimensionally crimped fibers, the proportion of the other fibers is preferably 1% to 50% by weight, more preferably 5% to 30% by weight, based on the total weight of the second fiber layer 22. Examples of the fibers constituting the first fiber layer 21 include general thermoplastic resin fibers, regenerated fibers such as rayon, and natural fibers such as cotton. The first fiber layer 21 may contain three-dimensionally crimped fibers.

The nonwoven fabric 13a is preferably produced as follows. First of all, Fiber aggregates that provide the first fiber layer 21 and the second fiber layer 22, respectively, are prepared. The fiber aggregate may be a web of fibers or a nonwoven fabric. Examples of the nonwoven fabric include air-through nonwovens, heat rolled (heat embossed) nonwovens, air-laid nonwovens, and melt-blown nonwovens. The web of fibers is prepared by, for example, carding. It is preferred to use a nonwoven fabric as a fiber aggregate providing the first fiber layer 21 and to use a web of fibers as a fiber aggregate providing the second fiber layer 22.

The web providing the second fiber layer 22 preferably contains self-crimping fibers. Self-crimping fibers can be handled before being heated in the same manner as usual fibers for nonwovens and, on being heated at a prescribed temperature, shrink to develop a three-dimensional helical crimp. Self-crimping fibers are exemplified by conjugate fibers having an eccentric sheath/core configuration or a side-by-side configuration having two thermoplastic polymer components having different shrinkage percentages. Examples of the self-crimping fibers that develop a three-dimensional crimp on heating include CPP (trade name) from Daiwabo Co., Ltd.

Consequently, a fiber aggregate providing the first fiber layer 21 is superposed on the fiber aggregate providing the second fiber layer 22, and the two plies are joined partially in a prescribed pattern. Various methods can be used to join the two plies as long as bonds 23 are formed in which at least the first fiber layer 21 is thinner than the other portions. For example, heat embossing or ultrasonic embossing is used preferably. The bonds 23 may be discrete dots or straight or curved (e.g., wavy) lines, grids, and zig-zags. The individual bonds 23 which are discrete dots may be circular, triangular, rectangular or any other shape. The dot-shaped bonds 23 can be arranged, for example, in a staggered pattern as shown in FIG. 5(a).

The first fiber layer 21 and the second fiber layer 22 joined together is heated to cause the self-crimping fibers present in the second fiber layer 22 to develop a helical crimp. Heating is achieved by, for example, blowing hot air in a through-air system. As a result of crimping, the fibers of the second fiber layer 22 located between the bonds 23 shrink, whereby the second fiber layer 22 shrinks in its planar directions. On the other hand, the fibers of the first fiber layer 21 do not shrink. The fibers of the first fiber layer 21 located between the bonds 23 have nowhere to move but in the thickness direction. As a result, the fibers of the first fiber layer 21 rise to form a number of protrusions 24 between the bonds 23 while leaving depressions 25 between the protrusions 24, i.e., at the positions corresponding to the bonds 23. Thus, the nonwoven fabric 13a having an uneven surface topography on the side of the first fiber layer 21 is obtained.

In the present invention, the first side 13 of the heat and steam generating sheet 10 may be formed by the nonwoven fabric 13a alone or a laminate of the nonwoven fabric 13a and a sheet material with a flat surface. The nonwoven fabric 13a may be used as superposed on the skin facing side of the sheet material with a flat surface. The nonwoven fabric defining the second side 14 is not particularly restricted. Commonly used nonwoven fabrics such as air-through nonwovens, spun-bonded nonwovens, hydroentangled nonwovens, chemical bonded nonwovens, and heat bonded nonwovens can be used.

The heat and steam generating member 11 put into the holder 12 contains an oxidizable metal, a reaction accelerator, an electrolyte, and water. The heat and steam generating member 11 has the form of heat generating sheet or powder. In the case when the heat generating member 11 is a heat generating sheet, it is preferably formed of a fibrous sheet containing an oxidizable metal, a reaction accelerator, a fibrous material, an electrolyte, and water. That is, the heat generating sheet is preferably a water-containing fibrous sheet containing an oxidizable metal, a reaction accelerator, a fibrous material, and an electrolyte. The heat generating sheet is more preferably a molded sheet containing an oxidizable metal, a reaction accelerator, and a fibrous material and having incorporated therein an aqueous electrolyte solution. The heat generating sheet is exemplified by a sheet formed by a wet papermaking technique and a laminate structure in which heat generating powder is held in between sheets of paper, etc. Such a heat generating sheet is produced by, for example, the wet papermaking process taught in commonly assigned JP 2003-102761A or extrusion using a die coater. In the case when the heat generating member 11 is a heat generating powder, it preferably includes an oxidizable metal, a reaction accelerator, a water retaining material, an electrolyte, and water. A heat generating sheet is preferred to a heat generating powder in terms of uniform application of steam to the eyes and its surroundings whatever posture a wearer takes. Furthermore, a heat generating sheet is advantageous over a heat generating powder in terms of ease of smoothing out the exothermic temperature and high ability to hold an oxidizable metal.

The heat generating member 11 which is a heat generating sheet is preferably a molded sheet made out of 60% to 90%, more preferably 70% to 85%, of an oxidizable metal, 5% to 25%, more preferably 8% to 15%, of a reaction accelerator, and 5% to 35%, more preferably 8% to 20%, of a fibrous material, all by weight, having incorporated therein 25 to 80 parts by weight, more preferably 30 to 70 parts by weight, per 100 parts by weight of the molded sheet, of a 1% to 15%, more preferably 2% to 10%, by weight aqueous solution of an electrolyte. The heat generating member 11 which is a heat generating powder is preferably a mixture of 20% to 80%, more preferably 20% to 50%, of an oxidizable metal, 1% to 25%, more preferably 5% to 20%, of a reaction accelerator, and 3% to 25% of a water retaining material, all by weight, having incorporated therein 0.3% to 12% by weight of an electrolyte and 20% to 60% by weight of water per 100 parts by weight of the solids content including the oxidizable metal, reaction accelerator, and water retaining material. The materials constituting the heat generating sheet or heat generating powder can be selected from those commonly used in the art. The materials described in JP 2003-102761A supra are useful as well.

The heat and steam generating sheet 10 of the present embodiment is packaged in a wrapper (not shown) made of an oxygen barrier material so as to protect the heat generating member 11 from coming into contact with air until use. Materials of such an oxygen barrier wrapper preferably include those having an oxygen transmission rate (ASTM D-3985) of 10 $cm^3 \cdot mm/(m^2 \cdot day \cdot MPa)$ or lower, more preferably 2 $cm^3 \cdot mm/(m^2 \cdot day \cdot MPa)$ or lower. Examples of the oxygen barrier wrapper include a film such as an ethylene-vinyl alcohol copolymer or polyacrylonitrile and a laminate of such a film and vacuum deposited ceramic or aluminum or the like.

The package is preferably labeled to indicate that the heat and steam generating sheet 10 relieves eyestrain and/or dry eye. For example, the package may be labeled to indicate that applying the heat and steam generating sheet to the eyes and its surroundings relieves eyestrain or dry eye thereby alleviating symptoms, such as blurred vision, hazy vision, indistinct vision. Consumers will be informed by this labeling that the heat and steam generating sheet of the present invention provides improvements on the near triad causative of reduction in vision that have heretofore been impossible with conventionally known disposable body warmers. Thus, the good value of the improved performance of the present invention will easily be recognized by consumers. The labeling can contain any kind of information means for conveying information about the improved performance to consumers, including signs and graphics as well as letters. The labeling may contain information to the effect that the product of the present invention is superior to other commercial products. In addition to, or in place of, the labeling on the package, instructions containing the contents of the labeling may be put in the package together with the heat and steam generating sheet 10. The heat and steam generating sheet 10 itself may directly be labeled.

Figure 8:
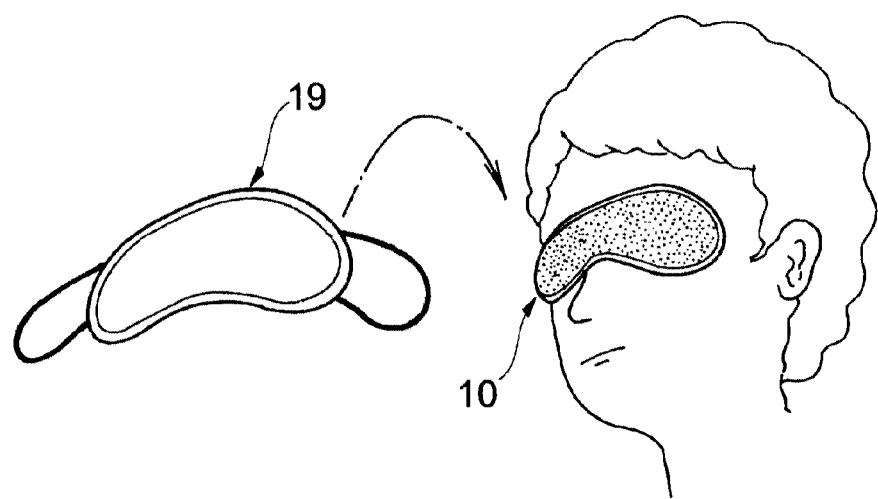
FIG. 8 illustrates a usage of the heat and steam generating sheet for eye application of FIG. 1.

The heat and steam generating sheet 10 taken out of the package can be used, for example, in combination with an eye mask 19 as shown in FIG. 8, in which the sheet 10 is inserted between the eye mask 19 and the eyes of a wearer. When used in that manner, heat and steam from the heat and steam generating sheet 10 can uniformly be applied to the skin of the wearer whatever posture (e.g., lying on the wearer's back or sitting) the wearer takes. This is advantageous for enabling use of the heat and steam generating sheet 10 in various situations. For example, one may wear the heat and steam generating sheet 10 while lying in one's home, or one may use the sheet 10 as soon as one feels eyestrain or eye dryness at a desk at work. Furthermore, one can wear the heat and steam generating sheet 10 easily even while travelling on a business trip by trains, planes, cars, etc.

Another preferred embodiment of the present invention will then be described with reference to FIGS. 9 and 10. The description on the foregoing embodiment applies to this embodiment unless otherwise specified. The heat and steam generating sheet 10 of the present embodiment has the same contour as that of the foregoing embodiment but is different from the foregoing embodiment in the shape of the space to put in the heat and steam generating member 11 as follows. The holder 12 has two annular seals 16 inside the peripheral seal 15 each providing a space in which a heat and steam generating member 11 is held. The sheet defining the first side 13 and the sheet defining the second side 14 are not joined to each other to provide a space therebetween in the area delineated by the peripheral seal 15 and the annular seals 16. That area is named a non-joined region 17. The non-joined region 17 surrounds the two heat and steam generating members 11.

The space formed in the non-joined region 17 functions as an air reservoir. The space also serves for regulating the steam generated from the heat and steam generating sheet 10. The region surrounding the heat and steam generating members 11 functions as an insulator against the heat generated from the heat and steam generating members 11. The space prevents the generated steam from being dissipated from the perimeter of the heat and steam generating sheet 10 and from coming into direct contact with the outer atmosphere. As a result, reduction in temperature of the steam supplied from the heat and steam generating sheet 10 to the skin of the wearer is suppressed.

Figure 9:
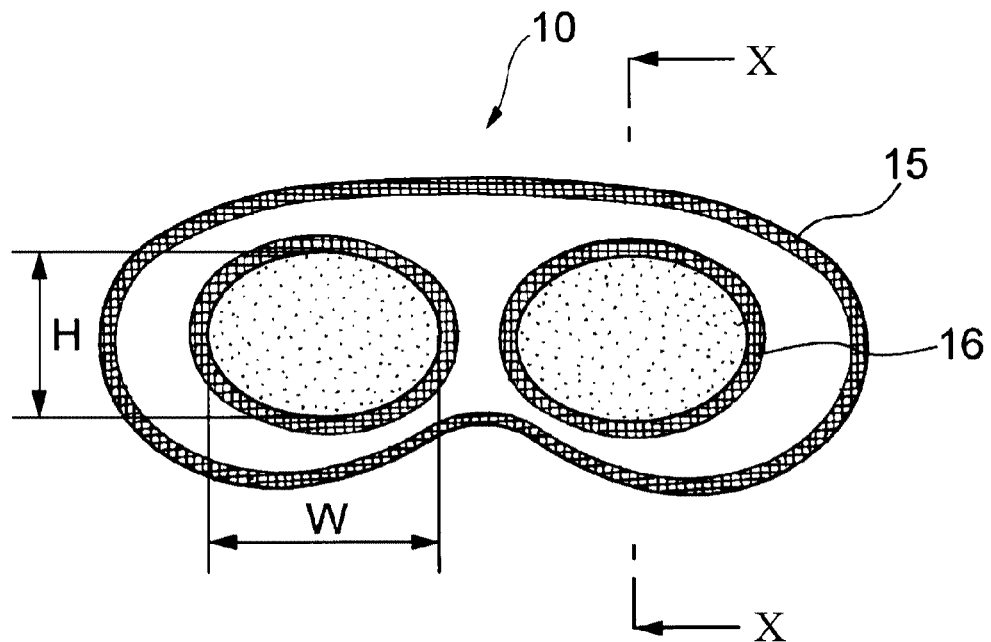
FIG. 9 is a plan of another embodiment of a heat and steam generating sheet for eye application according to the invention (equivalent to FIG. 1).
Figure 10:
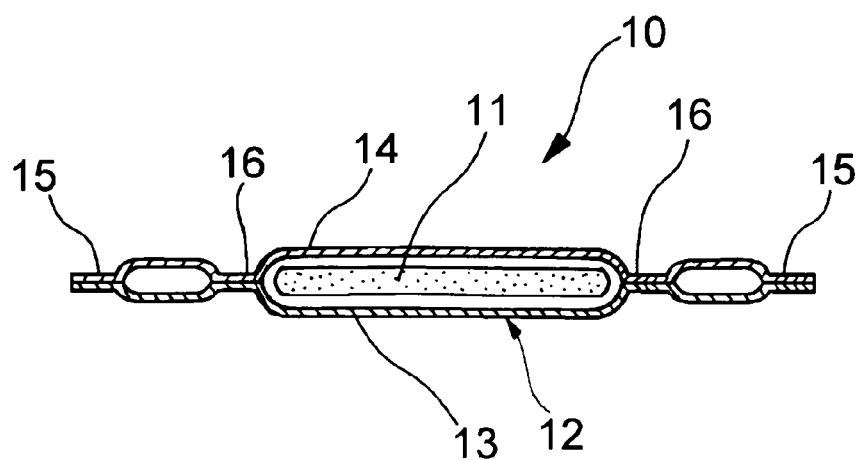
FIG. 10 is a cross-section taken along line X-X of FIG. 9.
Figure 11:
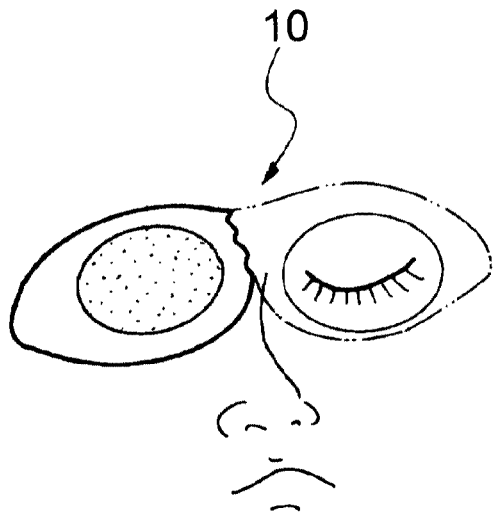
FIG. 11 is the heat and steam generating sheet for eye application of FIG. 9 while worn.

As illustrated in FIG. 9, the position of each annular seal 16 corresponds to each eye pit of a user wearing the heat and steam generating sheet 10. Each annular seal 16 has a length W in the horizontal direction larger than the distance between the wearer's inner and outer canthi and a length H in the vertical direction enough to cover the upper and lower eyelids closed over the wearer's eyeball. The heat and steam generating sheet is thus designed to apply heat and steam over a broad area of the eyes and its surroundings as drawn in FIG. 11. From this point of view, a plan view area of the space surrounded by each annular seal 16, i.e., the heat and steam generating member put into the space is preferably 1500 to 6000 $mm^2$, more preferably 1500 to 4000 $mm^2$, even more preferably 2000 to 3500 $mm^2$. From the same viewpoint, the length W in the horizontal direction is preferably 40 to 80 mm, more preferably 50 to 70 mm, and the length H in the vertical direction is preferably 30 to 100 mm, more preferably 30 to 70 mm, even more preferably 40 to 60 mm.

The space surrounded by the annular seal 16 may have any shape according to the shape of the heat and steam generating member to be held therein, such as an angular polygonal shape, e.g., a rectangle as illustrated in FIG. 12, a pentagon or a hexagon, as well as a circle or an elongated circle as illustrated in FIG. 9. While in FIG. 9 the holder 12 has two annular seals 16 corresponding to both eyes of a wearer, only one annular seal may be formed to provide a single space in which two heat and steam generating members are placed leaving a connecting space 65 therebetween unoccupied as illustrated in FIG. 12.

Similarly to the foregoing embodiment, the heat and steam generating sheet 10 of the present embodiment may have either a heat generating sheet or a heat generating powder held as a heat and steam generating member 11 in the holder 12. A heat generating sheet is preferred to a heat generating powder in terms of uniform application of heat and steam to the eyes and its surroundings whatever posture a wearer takes.

Figure 12A:
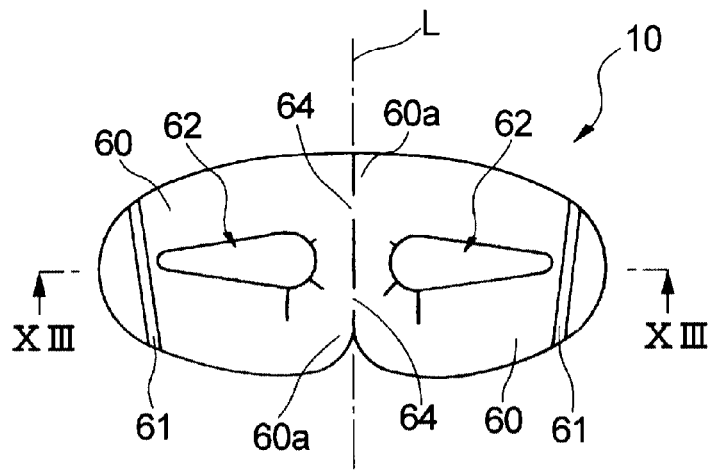
FIG. 12($a$) is a plan of still another embodiment of a heat and steam generating sheet for eye application according to the invention before use, seen from its first side, and FIG. 12($b$) is a plan of the same heat and steam generating sheet for eye application while in use, seen from its first side.
Figure 12B:
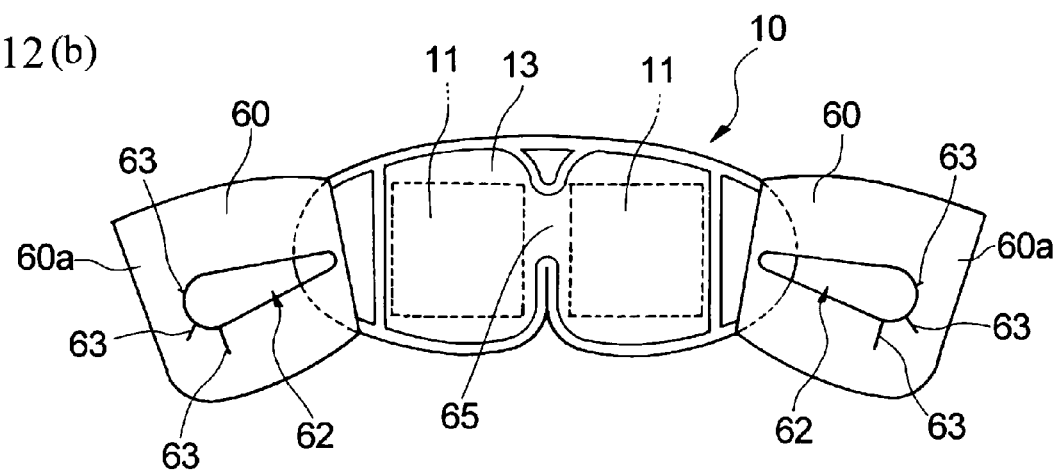

Still another embodiment of the present invention will be described by way of FIGS. 12(a) and 12(b). FIG. 12(a) is a plan of a heat and steam generating sheet 10 according to the present embodiment before use, seen from its first side, and FIG. 12(b) is a plan of the same heat and steam generating sheet 10 while in use, seen from its first side. The description on the foregoing embodiments applies to this embodiment unless otherwise described. The heat and steam generating sheet 10 of the present embodiment is used without the aid of an eye mask unlike those of the foregoing embodiments.

The heat and steam generating sheet 10 of the present embodiment has an ear loop 60 on both ends thereof. A pair of ear loops 60 are attached to both ends of the first side 13 of the sheet 10 by respective ear loop joints 61. Each ear loop joint 61 is a straight line extending inclined across the sheet 10 inboard of the lateral end of the sheet with its upper end positioned outboard of its lower end. Each ear loop 60 has the same shape as half the heat and steam generating sheet 10 divided by the vertical centerline L.

The ear loops 60 are disposed to cover the first side 13 of the heat and steam generating sheet 10 as illustrated in FIG. 12(a) until use. The upper and lower edges of the ear loops 60 are even with those of the heat and steam generating sheet 10. Thus, the heat and steam generating sheet 10 has its first side 13 protected with the ear loops 60 and kept clean until use. The ear loops 60 being so designed, there is an advantage that the holder 12 having heat generating member 10 held therein and the ear loops 60 attached thereto can be trimmed to shape at the same time.

Upon use, the ear loops 60 in the state before use shown in FIG. 12(a) are opened outward and downward along the respective ear loop joints 61 to make wing-like ear loops ready for use as illustrated in FIG. 12(b).

The ear loop 60 is formed of a sheet having an opening 62 cut. The opening 62 is generally an elongated circle extending in the lateral or horizontal direction of the heat and steam generating sheet 10 and tapered toward the ear loop joint 61. The ear loop 60 has slits 63 cut near its distal end 60a, each slit 63 being open to the opening 62. Each slit 63 opens to a varied degree depending on the size of the wearer's face to provide a snug fit against the wearer's face.

The ear loop 60 can be formed of any sheet selected from a stretchable sheet, an extensible but non-stretchable sheet, and an inextensible and non-stretchable sheet. Examples of the sheet include nonwoven fabrics, woven fabrics, papers, or resin films.

As shown in FIG. 12(a), a pair of the ear loops 60 before use partly connect to each other at their distal ends via a connecting part 64. The connecting part 64 is formed by, for example, perforations. The two ear loops 60 are seemingly integral with each other via the connecting part 64 and certainly cover the first side 13 of the heat and steam generating sheet 10 before use.

Figure 13:
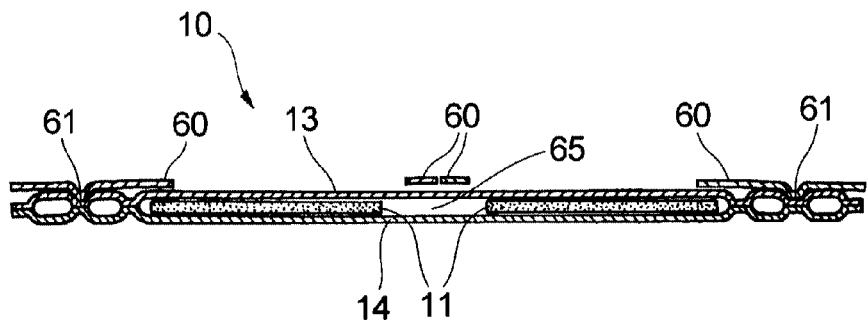
FIG. 13 is a cross-section taken along line XIII-XIII of FIG. 12($a$).

As shown in FIG. 12(b), the heat and steam generating sheet 10 of the present embodiment has a pair of rectangular heat and steam generating members 11 at positions corresponding to eyeballs. As illustrated in FIG. 13, a cross-section of FIG. 12(a), the spaces containing the respective heat and steam generating members 11 connect to each other to form a single space via a connecting space 65 located in the laterally middle part of the heat and steam generating sheet 10. The space contains two heat and steam generating members 11. As a result, air flows uniformly between the two heat and steam generating members 11 so that the heat and steam generating members 11 generate heat and steam uniformly.

While the present invention has been described based on its preferred embodiments, it should be understood that the invention is not deemed to be limited thereto. For instance, while the heat and steam generating sheets 1 of the embodiments shown in FIGS. 1 and 9 are used in combination with an eye mask, the ear loops 60 illustrated in FIGS. 12(a) and 12(b) may be attached to these sheets so that they can be used without an eye mask.

EXAMPLES

The present invention will now be illustrated in greater detail with reference to Examples, but it should be understood that the invention is not construed as being limited thereto. Unless otherwise noted, all the percents and parts are by weight.

Example 1

(1) Preparation of Heat Generating Sheet
Preparation of Slurry
(a) Oxidizable metal: iron powder (RKH (trade name) from Dowa Iron Powder Co., Ltd. 84%
(b) Fibrous material: pulp fiber NBKP (Mackenzie (trade name) from Fletcher Challenge Canada, Ltd.; CSF: 200 ml) 8%
(c) Activated carbon: average particle size 45 um, (Carboraffin (trade name) from Japan EnviroChemicals, Ltd.) 8%

To the mixture of components (a), (b), and (c) above were added 0.7 parts of a polyamide-epichlorohydrin resin (WS4020 from Seiko PMC Corp.) as a cationic flocculant and 0.18 parts of sodium carboxymethyl cellulose (HE1500 F from Dai-ichi Kogyo Seiyaku Co., Ltd.) as an anionic flocculant per 100 parts of the solid contents of the mixture (the total of compounds (a) to (c)). The mixture was then diluted with industrial water to a solids concentration of 12% to obtain slurry.

Papermaking Conditions
The slurry thus prepared was diluted with water to 0.3% in front of the head box and drained on an inclined short-wire paper machine at a line speed of 15 m/min to form a wet mat.
Dewatering and Drying Conditions
The wet mat was dewatered between felt blankets, passed as such between 140° C. heated rollers to be dried to a water content of 5% or less. The dried sheet had a basis weight of 450 g/m$^2$ and a thickness of 0.45 mm. As a result of measurement with a thermogravimetric analyzer (TG/DTA 6200 from Seiko Instruments Inc.), the resulting molded sheet was found to be made up of 84% iron, 8% activated carbon, and 8% pulp.
Preparation of Heat Generating Sheet
Two thicknesses of the resulting sheet were stacked on each other, and 50 parts of an electrolyte solution described below was syringed therein per 100 parts of the stack to impregnate throughout the stack by capillarity to give a heat generating member of sheet form (heat generating sheet).
Formulation of Electrolyte Solution
Electrolyte: purified salt (NaCl)
Water: industrial water
Electrolyte concentration: 5%
(2) Preparation of Heat and Steam Generating Sheet
A laminate of a PET spun-bonded nonwoven fabric, a PP melt-blown nonwoven fabric, and PP/rayon spun-bonded nonwoven fabric was used on the first side. The laminate had an air permeance of 0.01 sec, which is the detectable lower limit, and a WVTR of 12000 g/(m$^{20}$·24 hr). A composite including a moisture permeable, stretched porous polyethylene film containing calcium carbonate and a through-air nonwoven fabric was used on the second side with the through-air nonwoven fabric outside. The moisture permeable film had a basis weight of 45 g/m$^2$. The through-air nonwoven fabric was made up of sheath/core conjugate fibers having a polyethylene sheath and a polyethylene terephthalate core and had a basis weight of 20 g/m². The second side had an air permeance of 10000 sec/(100 ml·6.42 cm²) and a WVTR of 1000 g/(m²⁰·24 hr).

An eye mask-shaped holder shown in FIGS. 1 and 2 was made from the materials described above, and the heat generating sheet was put in the holder to make a heat and steam generating sheet. The heat and steam generating sheet had a stiffness of 0.4N/7 cm-width.

Figure 14:
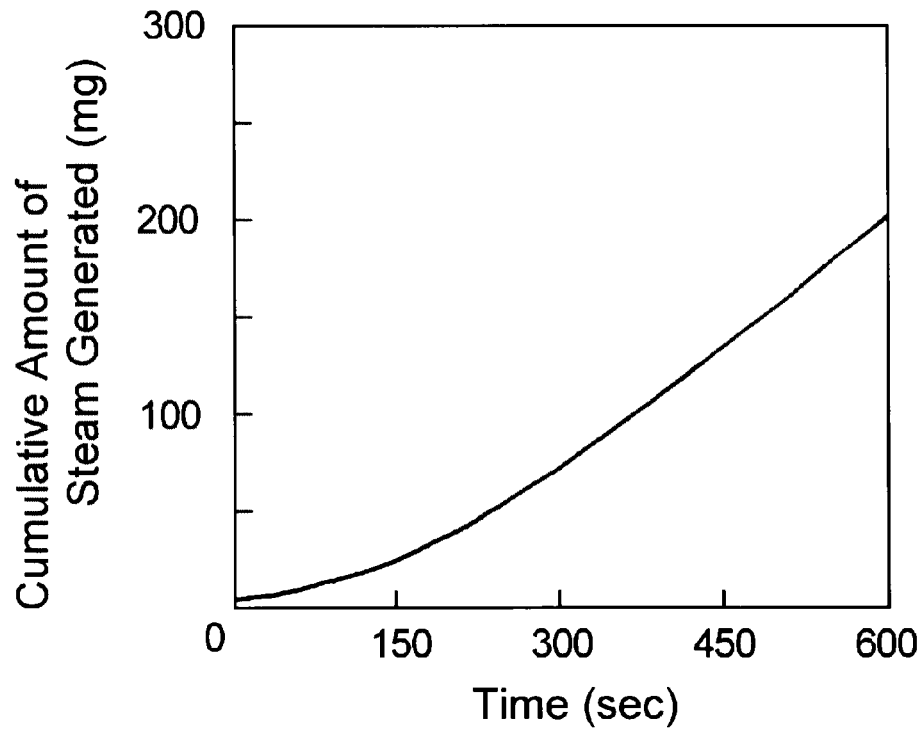
FIG. 14 is a graph showing steam generation from the heat and steam generating sheet for eye application obtained in Example 1.

The resulting heat and steam generating sheet had a heat and steam generation duration of 15 minutes as measured in accordance with the method described supra. The cumulative amount of steam released in 10 minutes from the start of heat generation is graphically shown in FIG. 14. The heat and steam generating sheet was worn by 3 male test subjects aged 39 to 43 (6 eyes), and the surface temperature of the skin to which the sheet was applied was measured in accordance with the method described supra. It was ascertained that the skin temperature was maintained at 37° C. to 40° C. over about 20 minutes in a measured environmental temperature of 25° C.

The effects of the heat and steam generating sheet on the accommodative power (subjective accommodative amplitude), pupillary response, and convergence response were determined. The heat and steam generating sheet was worn by 7 male test subjects aged 39 to 43 (14 eyes) (a) immediately after 2 hours of Video Display Terminal (hereinafter abbreviated as "VDT") work and (b) after a 10 minute application of the heat and steam generating sheet following 2 hours of VDT work. In the case (b), the heat and steam generating sheet was inserted between an eye mask and the eyes as illustrated in FIG. 8 and worn for 10 minutes. For control, measurements were taken after a 10 minute eye closure under an eye mask without using the heat and steam generating sheet. The accommodative power was measured with an accommodometer KOWA NP (trade name) from Kowa Company, Ltd., and the pupillary response and convergence response were measured using Tri-IRIS C9000 (trade name) from Hamamatsu Photonics K.K. The results obtained are shown in FIGS. 15 through 17.

Figure 15:
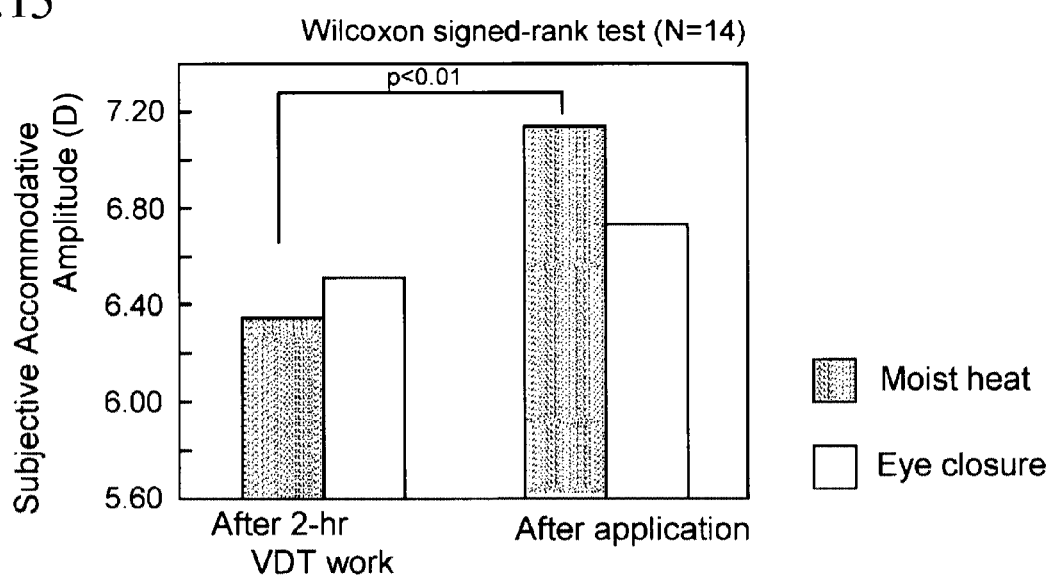
FIG. 15 is a graph showing the accommodation improving effect of the heat and steam generating sheet for eye application obtained in Example 1.

FIG. 15 shows the results of measurement of accommodation power (subjective accommodation). The ordinate indicates subjective accommodative amplitude represented by diopter (unit: D), the reciprocal of the near point (m). The larger the D value, the higher the accommodation power. It is generally said that the accommodative amplitude of adults is 10 D or higher in their twenties, 5 D in their thirties, and 3 D in their forties. As apparent from FIG. 15, it is seen that application of the heat and steam generating sheet brings about an increase of subjective accommodative amplitude, which indicates improvement on accommodation power with a significant difference.

Figure 16:
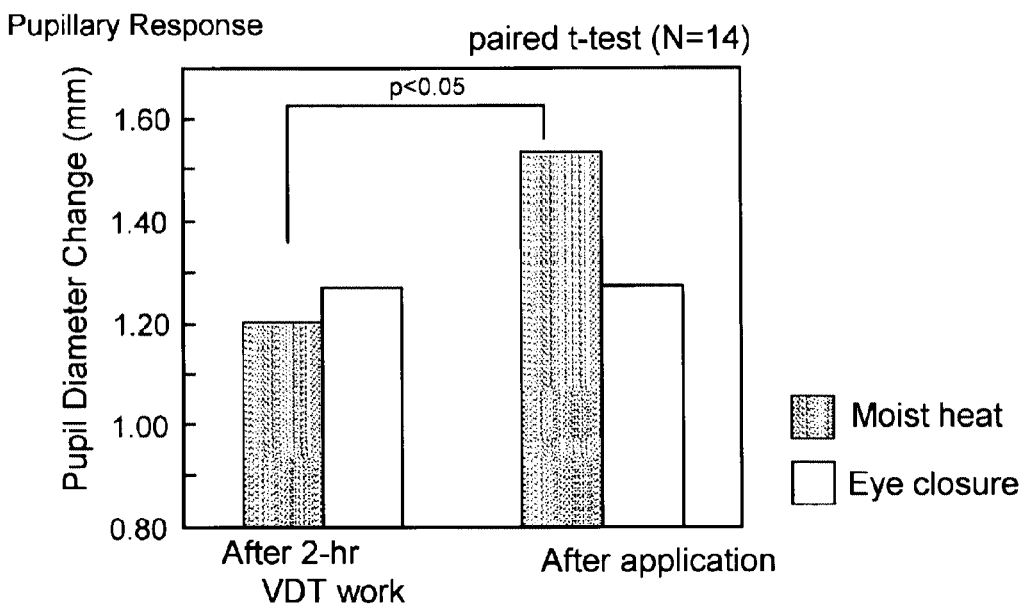
FIG. 16 is a graph showing the pupillary response improving effect of the heat and steam generating sheet for eye application obtained in Example 1.

FIG. 16 shows the results of pupil response measurement. The ordinate represents pupil diameter change (unit: mm), a change between mitotic pupil diameter and mydriatic pupil diameter obtained by continuously measuring the diameter of pupils in pursuit of a test object moving back and forth in front of the subject's eyes. The larger the pupil diameter change, the higher the pupil response. It is seen from the results in FIG. 16 that application of the heat and steam generating sheet brings about an increase of pupil diameter change, which indicates improvement on pupillary response with a significant difference.

Figure 17:
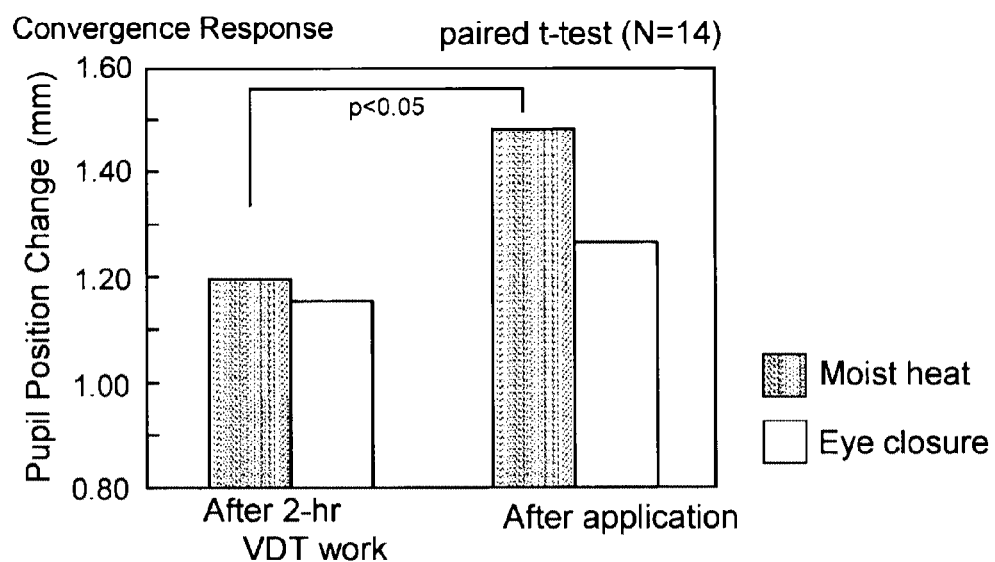
FIG. 17 is a graph showing the convergence response improving effect of the heat and steam generating sheet for eye application obtained in Example 1.

FIG. 17 shows the results of convergence response measurement. The ordinate represents pupil position change (unit: mm), an amount of change in pupil position as measured by continuously measuring the position of the pupils in pursuit of a test object moving back and forth in front of the subject's eyes. The larger the pupil position change, the higher the convergence response. It is seen from the results in FIG. 17 that application of the heat and steam generating sheet brings about an increase of moving distance of pupil position, which indicates improvement on convergence response with a significant difference.

Example 2

A heat and steam generating sheet illustrated in FIGS. 12(a) and 12(b) was obtained in the same manner as in Example 1, except for the following description.
(1) Preparation of Heat Generating Sheet A molded sheet was prepared in the same manner as in Example 1. A piece having an area of 26.95 cm² was cut out of the resulting molded sheet. Thirty-five parts of an electrolyte solution described below was syringed therein per 100 parts of the sheet to impregnate throughout the sheet by capillarity to obtain a heat generating sheet.
Formulation of Electrolyte Solution
Electrolyte: purified salt (NaCl)
Water: industrial water
Electrolyte concentration: 5%
(2) Preparation of Heat and Steam Generating Sheet A moisture permeable, stretched porous polyethylene film containing calcium carbonate was used on both the first and second sides of a holder. The moisture permeable film had a basis weight of 47 g/m², an air permeance of 8058 seconds, and a WVTR of 765 g/(m²·24 hr). The first side of the holder was formed of a laminate of the moisture permeable polyethylene film on the inner side thereof and a nonwoven fabric 13a of FIGS. 5(a) and 5(b) on the outer side thereof. The nonwoven fabric 13b was prepared in accordance with the method described supra. The nonwoven fabric 13a had a basis weight of 75 g/m², a thickness T1 of 1.8 mm at the protrusions and a thickness T2 of 0.5 mm at the depressions. The nonwoven fabric 13a comprises polyethylene terephthalate fiber layer as a first fiber layer 21 and polypropylene/polyethylene fiber layer as a second fiber layer 22. The second side of the holder was formed of a laminate of the moisture permeable polyethylene film on the inner side thereof and a spun-bonded nonwoven fabric on the outer side thereof. The spun-bonded nonwoven fabric was made up of sheath/core conjugate fiber having a polyethylene sheath and a polyethylene terephthalate core and had a basis weight of 30 g/m².

Example 3

A heat and steam generating sheet illustrated in FIGS. 12(a) and 12(b) was obtained in the same manner as in Example 2, except for the following description.
Preparation of Heat and Steam Generating Sheet A laminate of three thicknesses of a moisture permeable, stretched porous polyethylene film containing calcium carbonate and a nonwoven fabric of FIGS. 5(a) and 5(b) was used on the first side. The nonwoven fabric was the same as used in Example 2. The moisture permeable film had a basis weight of 20/m². The stack of three thicknesses of the moisture permeable film had an air permeance of 2583 seconds and a WVTR of 3496 g/(m²·24 hr). The second side was formed of an air impermeable, composite nonwoven fabric. The air impermeable composite nonwoven fabric comprises a nonwoven fabric made of sheath/core conjugate fiber having a polyethylene sheath and a polyester core and a polyethylene film heat-bonded to the nonwoven fabric. The basis weight of the composite nonwoven fabric was 65 g/m².

Example 4

A heat and steam generating sheet illustrated in FIGS. 12(a) and 12(b) was obtained in the same manner as in Example 2, except for the following description.

Preparation of Heat and Steam Generating Sheet

A laminate of two thicknesses of moisture permeable synthetic paper and a nonwoven fabric of FIGS. 5(a) and 5(b) was used on the first side. The nonwoven fabric was the same as used in Example 2. The moisture permeable synthetic paper had a basis weight of 40 g/m². The stack of two thicknesses of the moisture permeable synthetic fiber has a permeance of 135 seconds/(100 ml ·6.42 cm²) and a WVTR of 4760 g/(m²·24 hr). The same air impermeable composite nonwoven fabric as used in Example 3 was used on the second side.

The stiffness of the heat and steam generating sheets obtained in Examples 2 to 4 was measured in accordance with the method described above under conditions of a span of 80 mm and a crosshead speed of 20 mm/min. As a result, all the sheets were found to have a stiffness of 0.07N/7 cm-width when pressed down from the first side 13 and 0.08N/7 cm-width when pressed down from the second side 14.

Since the sheets of Examples 2 to 4 had two heat generating sheets discretely disposed for the respective eyes, each heat generating sheet was shorter than the span length 80 mm. Therefore, stiffness measurement under the above described conditions might fail to give the stiffness of the portion of the heat and steam generating sheet where the heat and steam generating member existed. Then, the accuracy of the measurement under the above conditions was confirmed by making the same measurement but with a span of 40 mm and at a crosshead speed of 5 mm/min. It is empirically known that a measured figure N obtained under conditions of 80 mm span and 20 mm/min crosshead speed and a measured figure A obtained under conditions of 40 mm span and 5 mm/min crosshead speed have equality (1):

$$N = A \times (1/2) \cdot (7/\text{sample width}) \quad (1)$$

The stiffness value calculated using equality (1) and the measured figure A obtained with a span of 40 mm and at a crosshead speed of 5 mm/min was 0.06N/7 cm-width. Accordingly, the measurement under the conditions of an 80 mm span and a 20 mm/min crosshead speed was confirmed to be accurate.

Each of the heat and steam generating sheets obtained in Examples 2 to 4 was worn by five male subjects aged 39 to 46 (10 eyes), and the temperature of the skin where the sheet was being applied was measured in accordance with the method described supra. The skin temperature was found kept at 37° C. to 40° C. over a period of about 20 minutes during application. Additionally, the duration of steam generation by the heat and steam generating sheets was measured in accordance with the method described supra. As a result, the durations of the heat and steam generating sheets of Example 2, 3, and 4 were 15 minutes, 20 minutes, and 20 minutes, respectively.

The heat and steam generating sheets obtained in Examples 2 to 4 were evaluated for improvements on tear film BUT (break-up time), near visual acuity, accommodation (subjective accommodative amplitude), pupillary response, and convergence response. Each of the heat and steam generating sheets was worn by 5 male test subjects aged 39 to 46 (10 eyes) (a) immediately after 3 to 4 hours of VDT work and (b) after a 10 minute application of the heat and steam generating sheet following 3 to 4 hours of VDT work. The measurements were made in the same manner as in Example 1. The near visual acuity of each eye was measured using a standard near visual acuity chart placed 30 cm away from the eye or corrected eye. The tear film BUT was the time interval (unit: second) between the last complete blink and the disruption of fluorescein-stained tear film measured with a stopwatch under slitlamp examination. The results of measurements were averaged and are shown in FIGS. 18 through 22.

Figure 18:
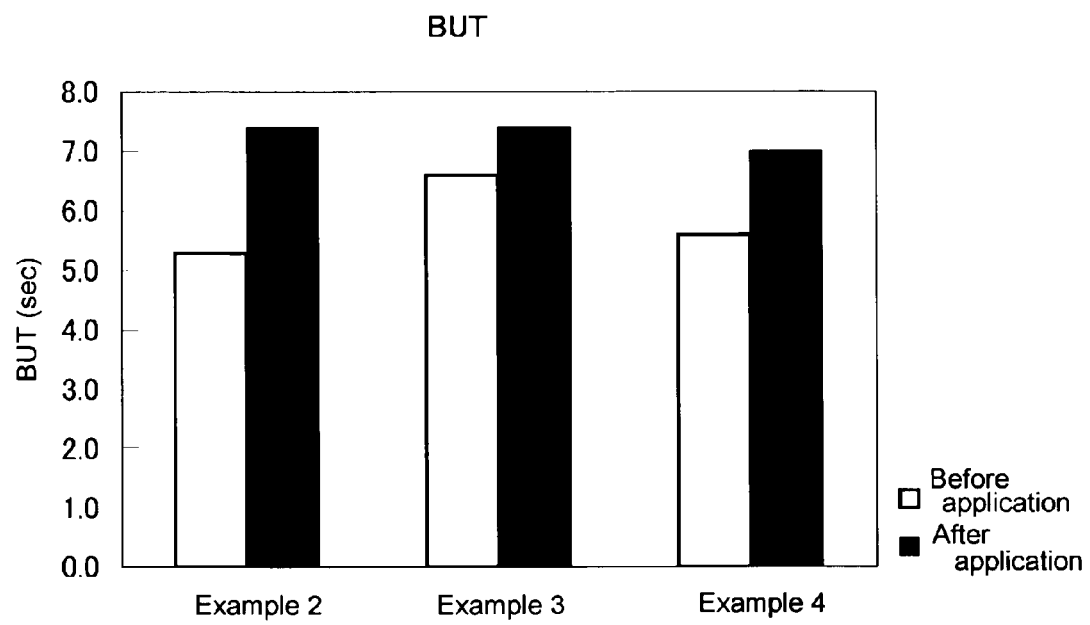
FIG. 18($a$) and FIG. 18($b$) are each a graph showing the BUT (break-up time) improving effect of the heat and steam generating sheets for eye application obtained in Examples 2 to 4.
Figure 18B:
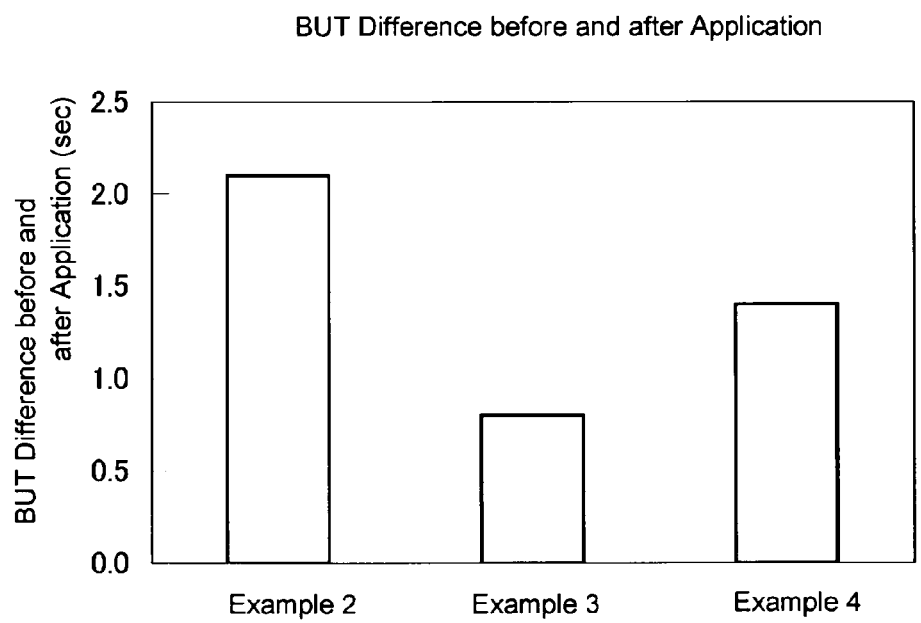

FIGS. 18(a) and 18(b) show the results of BUT (tear film break-up time on corneal surface) measurement. The BUT on the ordinate is the time in second between the last blink and appearance of a first break in the tear film. The larger the BUT value, the lower the eye dryness. BUT of normal eyes is generally 10 seconds or more. Eyes having a BUT of 5 seconds or less are diagnosed as dry eyes. It is seen from the results in those figures that application of the heat and steam generating sheet increases BUT, which indicates alleviation of dry eye conditions.

Figure 19A:
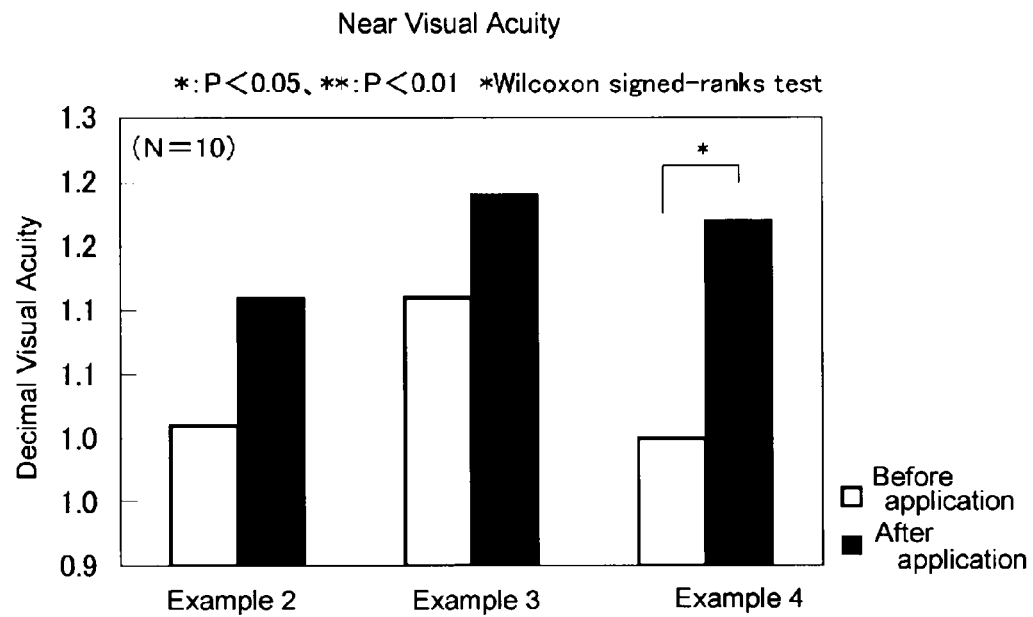
FIG. 19($a$) and FIG. 19($b$) are each a graph showing the near vision acuity improving effect of the heat and steam generating sheets for eye application obtained in Examples 2 to 4.
Figure 19B:
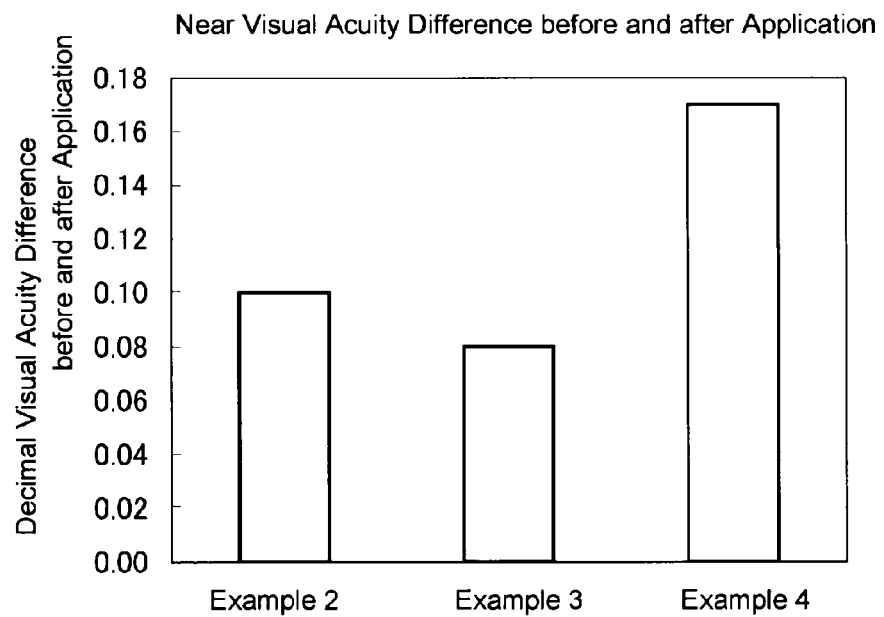

FIGS. 19(a) and 19(b) show the results of measurement of near visual acuity. As is apparent from those figures, application of the heat and steam generating sheet increases the subjective accommodation power, which indicates improvement on accommodation.

Figure 20A:
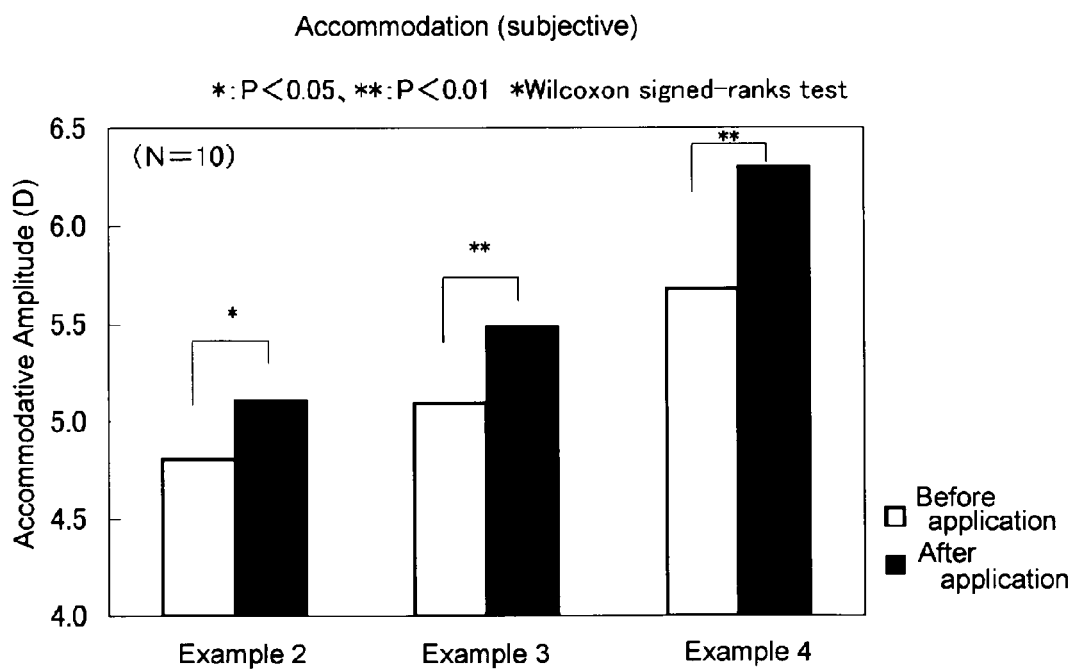
FIG. 20($a$) and FIG. 20($b$) are each a graph showing the accommodation improving effect of the heat and steam generating sheets for eye application obtained in Examples 2 to 4.
Figure 20B:
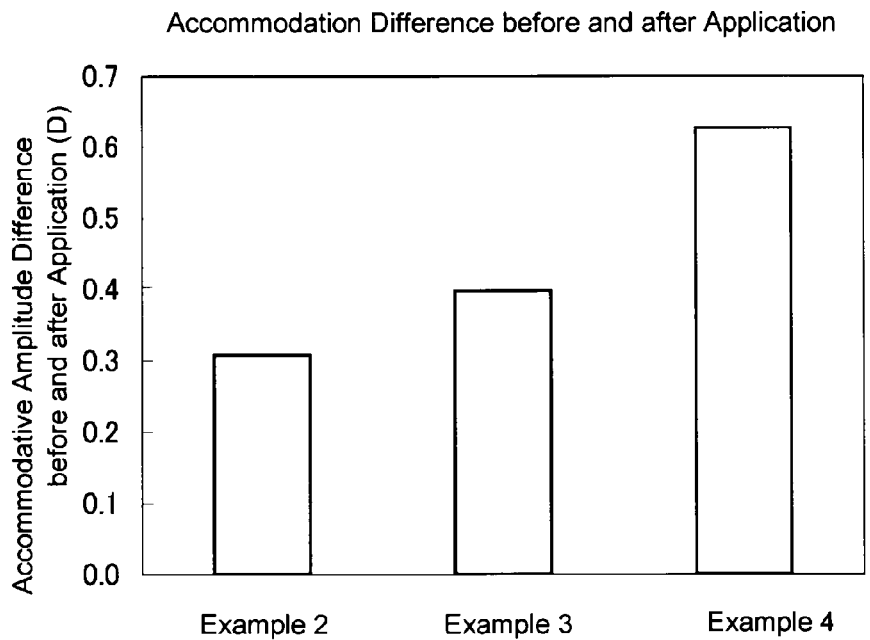

FIGS. 20(a) and 20(b) show the results of measurement of accommodation (subjective accommodative amplitude). As is apparent from those figures, application of the heat and steam generating sheet increases the subjective accommodative amplitude, indicating improvement of accommodation with a significant difference.

Figure 21A:
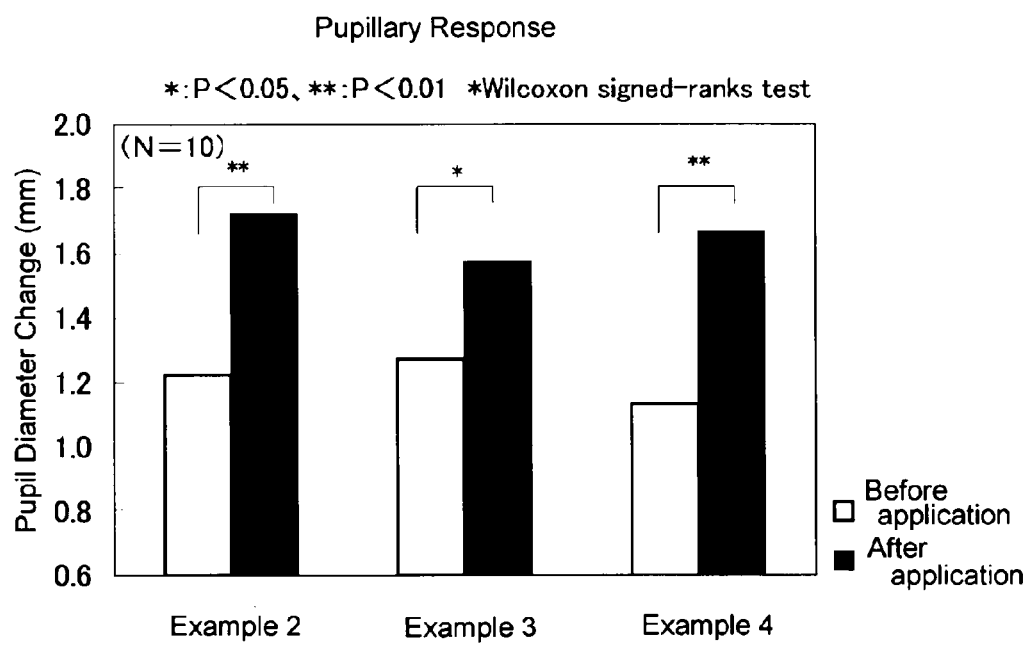
FIG. 21($a$) and FIG. 21($b$) are each a graph showing the pupillary response improving effect of the heat and steam generating sheets for eye application obtained in Examples 2 to 4.
Figure 21B:
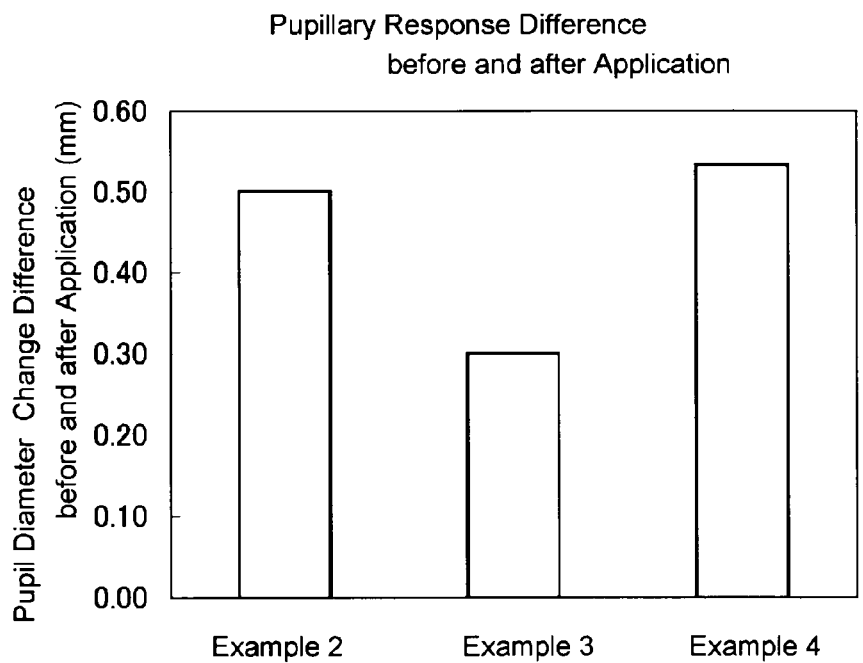

FIGS. 21(a) and 21(b) show the results of pupillary response measurement. The ordinate indicates pupil diameter change in mm. As is apparent from those figures, application of the heat and steam generating sheet increases the pupil diameter change, which indicates that the pupillary response was improved with a significant difference.

Figure 22A:
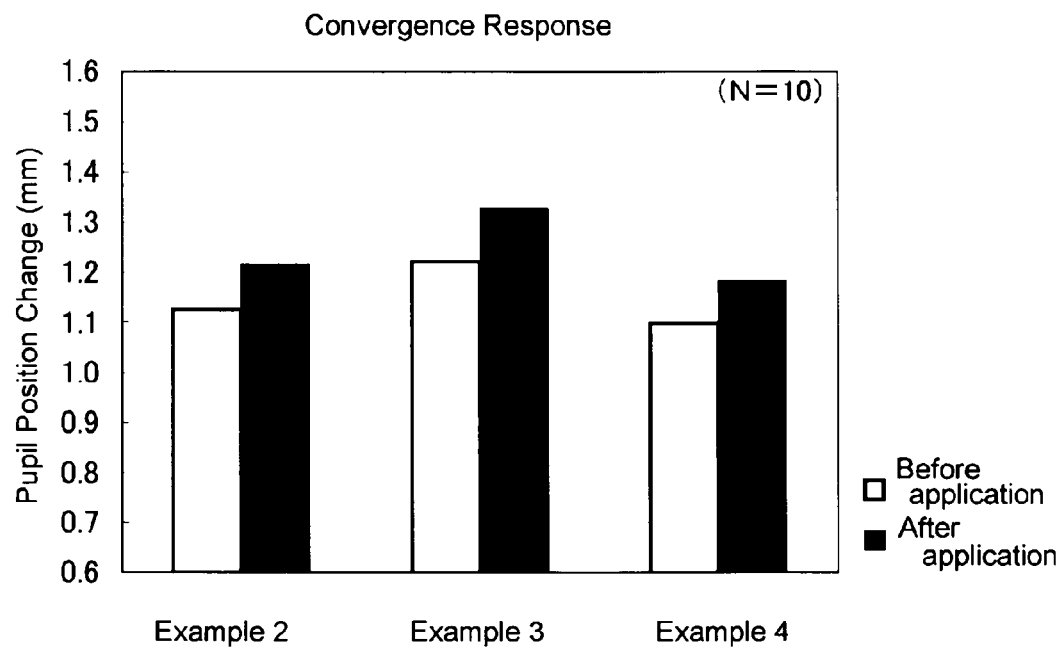
FIG. 22($a$) and FIG. 22($b$) are each a graph showing the convergence response improving effect of the heat and steam generating sheets for eye application obtained in Examples 2 to 4.
Figure 22B:
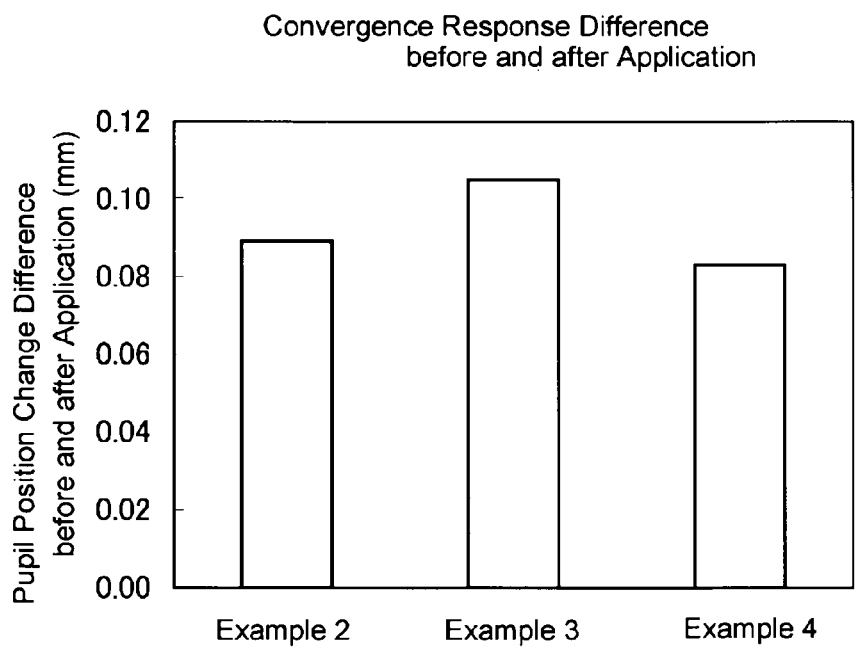

FIGS. 22(a) and 22(b) show the results of convergence response measurement. As is apparent from those figures, application of the heat and steam generating sheet increases the pupil position change, which indicates that the convergence response was improved.

The results shown in FIGS. 15 through 22 prove that application of the heat and steam generating sheet is effective in improving the near triad (accommodation, convergence, and pupillary constriction) which causes reduction in vision and improving tear film BUT (the time between blink and disruption of tear film on corneal surface) which causes dry eyes.

Industrial Applicability

As described, the heat and steam generator for eye application according to the present invention is effective in improving the near triad, i.e., reduction of accommodation, reduction of pupillary response, and convergence response abnormality. The heat and steam generator for eye application according to the invention is also effective in improving dry eye conditions attributed to insufficient tear film formation on the corneal surface due to obstruction of meibomian glands.

The invention claimed is:

1. A heat and steam generator for eye application comprising:
   a holder holding a heat and steam generating member containing an oxidizable metal which generates heat and steam by making use of an oxidative reaction of the oxidizable metal, the heat and steam generator being designed to supply steam to eyes and its surroundings,
   wherein the heat and steam generator releases steam from its side adapted to face the eyes and its surroundings for a period of 1 to 30 minutes to maintain the surface temperature of the skin which it faces at 34° C. to 43° C. over a period of 1 to 120 minutes, wherein the holder and the heat and steam generating member form a structure having a stiffness of 0.01 to 10 N/7cm-width, as measured by supporting a portion of the holder, which holds the heat and steam generating member, at opposing ends of the portion of the holder which extend in a vertical direction of the holder, and measuring a maximum resistance encountered by a platy penetrator blade which contacts a central the portion of the holder, and wherein a span of a specimen of the holder used for measuring the stiffness is 80 mm, the platy penetrator blade has a width of 50 mm and a tip radius of 5 mm, a crosshead speed of the platy penetrator blade is 20 mm/min, and, for measuring, the width of the platy penetrator blade coincides with the vertical direction of the holder.

2. The heat and steam generator for eye application according to claim 1, wherein the holder is a flat holder in which the heat and steam generating member is held, the holder having a first air permeable side and a second air permeable side opposite to the first air permeable side and being designed to release steam from at least one of the first and second air permeable sides that faces the eyes and its surroundings.

3. The heat and steam generator for eye application according to claim 2, wherein the second side has an air permeance (JIS P8117) equal to or higher than that of the first side, and wherein the heat and steam generator is designed to release steam through the first side.

4. The heat and steam generator for eye application according to claim 3, wherein the first side has an air permeance of 0.01 to 15000 seconds, and the second side has an air permeance of 100 to 60000 seconds.

5. The heat and steam generator for eye application according to claim 1, wherein the first side has a water vapor transmission rate of 100 g/(m²·24 hr) or more.

6. The heat and steam generator for eye application according to claim 1, wherein the holder is a flat holder in which the heat and steam generating member is held, the holder having an air permeable side and an air impermeable side opposite to the air permeable side and being designed to release steam from the air permeable side.

7. The heat and steam generator for eye application according to claim 6, wherein the air permeable side has a water vapor transmission rate of 100 to 20000 g/(m²·24 hr).

8. The heat and steam generator for eye application according to claim 1, wherein the heat and steam generating member comprises a heat generating sheet capable of generating heat on contact with air, the heat generating sheet comprising a molded sheet containing an oxidizable metal, a reaction accelerator, and a fibrous material and an aqueous electrolyte solution incorporated into the molded sheet.

9. The heat and steam generator for eye application according to claim 1, further comprising an ear loop on both ends thereof.

10. The heat and steam generator for eye application according to claim 1, which is used in combination with an eye mask as inserted between the eye mask and wearer's eyes.

11. The heat and steam generator for eye application according to claim 1, which has a label indicating that it relieves eyestrain and/or dry eye or which is put in a package having the label.

12. The heat and steam generator for eye application according to claim 1, wherein the holder has a stiffness of 0.03 to 8 N/7cm-width.

13. The heat and steam generator for eye application according to claim 1, wherein the holder has a stiffness of 0.05 to 5 N/7cm-width.

14. The heat and steam generator for eye application according to claim 1,
wherein
the holder has a first side that is to face the skin and a second side which faces an opposing direction, and
the first and second sides are joined at a peripheral seal and at two annular seals which are located within the peripheral seal.

15. The heat and steam generator for eye application according to claim 14, wherein the two annular seals provide respective spaces in which heat and steam generating members are held so as to be separated by the two annular seals.

16. The heat and steam generator for eye application according to claim 1,
wherein
the holder has spaces in which a pair of heat and steam generating members are contained, and
the spaces of the holder are connected to each other to form a single space via a connecting space located in a lateral middle portion of the heat and steam generator so that the single space contains the pair of heat and steam generating members.

17. The heat and steam generator for eye application according to claim 1, further comprising:
ear loops at both ends of the heat and steam generator which are attached by ear loop joints, wherein each ear loop joint extends at an inclination across the heat and steam generator inboard of a lateral end of the heat and steam generator with an upper end thereof positioned outboard of a lower end thereof.

18. The heat and steam generator for eye application according to claim 1, wherein a surface of the heat and steam generator to which the eyes and its surroundings are brought into contact include a non-woven fabric which contains three-dimensionally crimped fibers.

* * * * *